United States Patent
Niewels et al.

(10) Patent No.: US 7,393,198 B2
(45) Date of Patent: Jul. 1, 2008

(54) MOLDING-SYSTEM VISCOUS-DRAG SENSOR

(75) Inventors: Joachim Johannes Niewels, Thornton (CA); Omeir Shahid Ansari, Markham (CA); William Cornelius Janzen, Mississauga (CA); Michael Keith Zuraw, Georgetown (CA); Nenad Miljkovic, Mississauga (CA)

(73) Assignee: Husky Injection Molding Systems Ltd., Bolton, Ontario (CA)

( * ) Notice: Subject to any disclaimer, the term of this patent is extended or adjusted under 35 U.S.C. 154(b) by 42 days.

(21) Appl. No.: 11/495,496

(22) Filed: Jul. 28, 2006

(65) Prior Publication Data

US 2008/0023862 A1 Jan. 31, 2008

(51) Int. Cl.
*B29C 45/23* (2006.01)
*B29C 45/76* (2006.01)

(52) U.S. Cl. ...................................... 425/145; 425/562

(58) Field of Classification Search ................. 425/145, 425/562
See application file for complete search history.

(56) References Cited

U.S. PATENT DOCUMENTS

| | | | |
|---|---|---|---|
| 3,863,001 A | 1/1975 | Thumudo | |
| 3,969,055 A | 7/1976 | Buckethal | |
| 4,965,028 A | 10/1990 | Maus et al. | |
| 5,069,403 A | 12/1991 | Marentic et al. | |
| 5,192,556 A | 3/1993 | Schmidt | |
| 5,421,715 A | 6/1995 | Hofstetter et al. | |
| 5,527,499 A | 6/1996 | Miley | |
| 5,683,731 A | 11/1997 | Deardurff et al. | |
| 5,688,462 A | 11/1997 | Salamon et al. | |
| 6,254,377 B1* | 7/2001 | Kazmer et al. | ............... 425/562 |
| 6,343,922 B1 | 2/2002 | Kazmer et al. | |
| 6,382,528 B1 | 5/2002 | Bouti | |
| 6,544,028 B2 | 4/2003 | Wright et al. | |
| 6,572,361 B2 | 6/2003 | Gould et al. | |
| 6,575,729 B2 | 6/2003 | Godwin et al. | |
| 6,923,638 B2 | 8/2005 | Chen | |
| 2002/0149135 A1 | 10/2002 | Choi et al. | |
| 2004/0130062 A1 | 7/2004 | Sicilia | |
| 2004/0256768 A1 | 12/2004 | Olaru | |
| 2007/0132146 A1* | 6/2007 | Klobucar | .................. 264/328.1 |

FOREIGN PATENT DOCUMENTS

| CA | 2457643 A1 | 8/2004 |
|---|---|---|
| JP | 10323874 A | 12/1998 |

* cited by examiner

*Primary Examiner*—Robert B Davis

(57) ABSTRACT

A molding system having a melt pathway configured to convey a molding material. The molding system includes a viscous-drag sensor having: (i) a pathway blockage, and (ii) an actuator. The viscous-drag sensor is interactable with the molding material. The pathway blockage is movable along the melt pathway. The pathway blockage is movable along a first direction to further open the melt pathway. The pathway blockage is movable along a second direction to further close the melt pathway. The actuator is coupled with the pathway blockage. The actuator biases the pathway blockage to vary the melt pathway while the molding material drags along and moves the pathway blockage. Responsive to the pathway blockage sensing viscous-drag force, the pathway blocks acts to: (i) further open the melt pathway if a viscosity of the molding material is high, and (ii) further close the melt pathway if the viscosity of the molding material is low.

34 Claims, 10 Drawing Sheets

MOLDING-SYSTEM VISCOUS-DRAG SENSOR

TECHNICAL FIELD

The present invention generally relates to, but is not limited to, molding systems, and more specifically the present invention relates to, but is not limited to, (i) a molding system, including a viscous-drag sensor interactable with a molding material flowable along a melt pathway and/or (ii) a method of a molding-system, amongst other things.

BACKGROUND

Examples of known molding systems are the: (i) HyPET™ Molding System, (ii) Quadloc™ Molding System, (iii) Hylectric™ Molding System, and (iv) HyMet™ Molding System, all manufactured by Husky Injection Molding Systems Limited (Location: Bolton, Ontario, Canada; WWW-URL: www.husky.ca).

U.S. Pat. No. 3,863,001 (Inventor: Thumudo; Published: 1975 Jan. 28) discloses an improvement in a method of making a generally flat circular transfer preform from a polymeric extrudate. The method includes steps (a), (b) and (c). Step (a) includes an improved breaker plate that has oppositely disposed surfaces, and each of the surfaces generally defines a portion of a sphere, a center of curvature and a radius of curvature. The centers of curvature are both located on the upstream side of the breaker plate. The plate defines a plurality of orifices that extend through the plate and cover a major portion of the surface area of the plate. The orifices nearer the center of the plate are longer than those nearer the periphery, to compensate for the frictional drag exerted on the extrudate by the surface of the barrel. Step (b) includes forcing the extrudate through the improved breaker plate thereby forming a plurality of individual extrusions. Step (c) includes permitting the individual extrusions to nest together.

U.S. Pat. No. 3,969,055 (Inventor: Buckethal; Published: 1976 Jul. 13) discloses a system and method for controlling the injection of material through two or more gates into the cavity of injection-molding apparatus. In this system, a sensor develops an indication of unbalanced flow conditions produced by the injection of the material into the cavity of the mold. A regulator also forms part of the system and serves to adjust the relative amounts of material passing through the gates. The method includes sensing unbalanced flow conditions produced by the material injected into the cavity and adjusting the relative amounts of materials injected into the cavity through the various gates.

U.S. Pat. No. 4,965,028 (Inventor: Maus et al; Published: 1990 Oct. 23) discloses a method for improving a thermoplastic's melt quality and increasing melt temperature entering a gate of each cavity of a multicavity mold and thereby improving molded part quality. The improvement is achieved by steps (a), (b), (c) and (d). Step (a) includes injecting a plasticated melt under pressure through a nozzle seated in a sprue bushing into a multicavity moldset, melt-delivery system. The delivery system includes melt passageways maintained continuously in fluid communication between the sprue bushing on an upstream end. Runner bushings feed into each mold cavity on a downstream end. The melt contained in the delivery system is intermittently pressurized and depressurized with each injection cycle. The melt always retains sufficient fluidity to flow as required when next pressurized. Step (b) includes displacing the melt contained in the delivery system downstream toward the mold cavities. Upon each cycle's melt pressurization, the melt must pass through en route melt conditioning elements located upstream of each gate and downstream of each melt passageway. Each conditioning element consists of a male device member. The male device is generally torpedo shaped, and housed concentrically within a generally cylindrically shaped female bushing member. The conditioning element also includes a precisely dimensioned annular clearance space between the male and female members. Each conditioning element defines at least one inlet melt channel which is substantially blocked at its downstream end and at least one outlet melt channel which is substantially blocked at its upstream end. The inlet and outlet melt channels are maintained in fluid communication through the precisely dimensioned clearance space, such that melt transferring between the inlet and outlet melt channels must pass over the constrictive land. Furthermore, the melt transferring therebetween must undergo substantial angular change in flow direction as the inlet and outlet melt channels are not coaxially aligned. Each melt conditioning element feeds the melt directly into the gate. Step (c) includes shearing the melt as it flows during the intermittent pressurization of each cycle, thereby increasing the melt temperature and mixing the melt by angular flow direction change as the melt is transferred through the melt conditioning elements. Step (d) includes heating at least one of the male and female members of each melt conditioning element to a temperature greater than a temperature of the melt measured upstream of the melt conditioning elements. Forcing intimate contact between the melt and the heated members thereby increasing heat transfer between the melt and the heated members and increasing melt temperature downstream of the melt conditioning elements. This results in the melt entering each mold cavity to have substantially greater homogeneity, fluidity, and heat content with very minimally increased heat history.

U.S. Pat. No. 5,069,403 (Inventors: Marentic and Morris; Published: 1991 Dec. 03) discloses a method for providing a drag reduction article. The method includes three steps: (a), (b) and (c). Step (a) includes applying a layer of a first radiation curable composition to a carrier. Step (b) includes forming a first patterned surface on the radiation curable composition. Step (c) includes curing the first radiation curable composition by exposure to activating radiation to provide a first cured patterned surface that is capable of reducing drag resistance (that is, when a fluid flows thereacross).

U.S. Pat. No. 5,192,556 (Inventor: Schmidt; Published: 1993 Mar. 09) discloses a plastic molding apparatus for delivering a melt stream of moldable plastic material under pressure through a flow passageway and into a mold cavity. The apparatus includes a distributing plate having a distribution channel for conveying a plastic melt. A nozzle has a nozzle channel that communicates with the distribution channel. A mold cavity communicates with the nozzle channel. The mold cavity includes a connecting channel that connects the distribution channel with the nozzle channel. The connecting channel includes a flow entry portion, a reservoir portion and a flow restriction portion. The melt flows from the distribution channel to the flow entry portion, to the reservoir portion, to the flow restriction portion, and to the nozzle channel. The flow entry portion comprises a varying height channel that distributes the melt substantially equally. The reservoir portion has a larger capacity than the flow restriction portion so that the flow restriction portion holds back the melt flow from the reservoir portion. The connecting channel substantially equalizes flow pressure and flow velocity of the plastic melt to the nozzle channel.

U.S. Pat. No. 5,421,715 (Inventor: Hofstetter et al; Published: 1995 Jun. 06) discloses an apparatus for the simultaneous production of preforms, consisting of polyethylene terephthalate (PET) fed and distributed to a plurality of cavities. In order to reduce the occurrence of acetaldehyde formation in a cavity, for example, a heated distributor block used in the production of preforms of the PET material, the material flowing through a channel is subjected to additional turbulence. To this end, an element, preferably of metal, is installed in the channels, such element being provided with sets of radial spokes which are azimuthally offset in relation to each other in the axial direction. Besides inducing turbulence, such spokes act as homogenizing elements serving to diffuse heat over the cross section of the flowing process material.

U.S. Pat. No. 5,527,499 (Inventor: Miley; Published: 1996 Jun. 18) discloses an extrusion apparatus for producing a composite profile strip. The apparatus includes an extrusion head that has flow channels extending to an extrusion die. At least two extruders feed respective components at respective different pressures into the flow channels for passage to the extrusion die. The extrusion die has a common die outlet from which the components are discharged to form the composite profile strip. Respective flow restriction devices are disposed in the flow channels between the extruders and the extrusion die. The flow restriction devices are operative to decrease a difference in pressure between the components at the extrusion die to about 250 psi (pounds-per-square inch) or less prior to the components being brought together.

U.S. Pat. No. 6,343,922 (Inventors: Kazmer and Moss; Published: 2002 Feb. 05) discloses an injection molding apparatus. The apparatus including four components: (a), (b), (c) and (d). Component (a) is a manifold that has an inlet for receiving material injected from an injection molding machine. Component (b) is a plurality of injection nozzles coupled to the manifold for distributing the material to a corresponding plurality of gates to one or more mold cavities. Component (c) is a plurality of sensors respectively coupled to each of the plurality of nozzles, each sensor to sense a condition related to the rate of material flow at a location between the inlet and the plurality of gates. The last component (d) a controller to individually control respective rates at which material flows out of each of the plurality of injection molding nozzles and into the one or more cavities based on signals the controller receives from the plurality of sensors.

U.S. Pat. No. 5,683,731 (Inventor: Deardurff et al; Published: 1997 Nov. 04) discloses a redistributing device for use with melt flow exhibiting boundary layer and centralized flow. The device includes: (i) a body including a melt flow inlet end and a plurality of melt-flow outlets, said body engaging a melt flow channel, (ii) first means in said body for distributing at least said boundary layer among said plurality of melt flow outlets, (iii) second means in said body for distributing at least said centralized flow among said plurality of melt flow outlets, wherein said body has a central opening therein defining a central flow channel in fluid communication with said outlets comprising said second means for distributing, and said first means for distributing comprises inlets leading to a plurality of diverters positioned on said body and adjacent said opening, said diverters extending from said inlet end and into fluid communication with said plurality of melt-flow outlets, and wherein the material flowing in the central channel meets the material flowing in the diverters and emerges at the outlets.

U.S. Pat. No. 5,688,462 (Inventor: Salamon et al; Published: 1997 Nov. 18) discloses, in an injection molding process for making thermoplastic articles, an in-runner static mixer that is positioned near the gate to a mold cavity to mix molten thermoplastic such that said thermoplastic exiting the in-runner static mixer is more homogeneous with respect to temperature than that entering the in-runner static mixer. Passing the more homogeneously mixed molten thermoplastic through the gate to the mold cavity and allowing said cavity to fill and thermoplastic to cool, will result in an article aesthetically superior to one made by a process where no in-runner static mixing device is employed.

U.S. patent application Ser. No. 2002/0,149,135 (Inventor: Choi et al; Published: 2002 Oct. 17) discloses a multiple cavity injection molding system. The system includes a feed source that provides flowable polymeric material at conditions suitable for producing molded products therefrom. Mold cavities are adapted to receive flowable polymeric material from the feed source and produce molded products. A primary sprue extends from the feed source. A runner system extends between and providing fluid communication between the primary sprue and the plurality of mold cavities. The runner system has a feed inlet in communication with the primary sprue and a plurality of discharge ports in communication with the mold cavities. The runner system has a symmetrical configuration with respect to the primary sprue. The runner system includes at least two turbulence-inducing components. The turbulence components are selected from the group consisting of turbulence-inducing runners, turbulence-inducing steps, and turbulence-inducing angles. Upon performing an injection molding operation, the shear rate of polymeric material exiting the runner system is at least 50% of the shear rate of the polymeric material entering the runner system at the feed inlet.

U.S. Pat. No. 6,382,528 (Inventor: Bouti; Published: 2002 May 07) discloses, in an injection molding machine, a mixer that reduces the flow imbalances inherent in the melt as the flow branches within a manifold or other part of the injection machine. The mixer increase melt homogeneity by gradually mixing and changing the melt flow from all helical flow to all annular flow. The mixer provides an improved means for reducing flow imbalances that results in the elimination of weld lines and other part non-uniformities.

U.S. Pat. No. 6,544,028 (Inventor Wright et al; Published: 2003 Apr. 08) discloses a mixer method and apparatus for use generally in injection molding machines. The apparatus and method is generally comprised of a mixer insert that retains a mixing element that is sealingly inserted in the injection molding machine, for example a hot runner manifold. The mixing element reduces the melt imbalances in a flowing melt stream for the formation of improved molded parts.

U.S. Pat. No. 6,572,361 (Inventor: Gould et al; Published: 2003 Jun. 03) discloses a hot runner subsystem for an injection molding machine. The hot runner subsystem includes (i) a heated manifold having at least one primary melt channel disposed therein, (ii) an adapter plate rigidly affixed to said manifold, said adapter plate having at least one first melt channel communicating with said at least one primary melt channel, and (iii) a mixer having an inlet and an exit, said inlet communicating with said first melt channel, and said exit communicating with a secondary melt channel.

U.S. Pat. No. 6,575,729 (Inventor: Godwin et al; Published: 2003 Jun. 10) discloses a heater for an injection molding runner nozzle. The heater includes a cylindrical, heat-conducting band substrate adapted to be placed over an outer surface of the nozzle. A first dielectric layer directly is deposited on an outer cylindrical surface of the band. A conductive-ink resistive heating element is directly deposited on the first dielectric layer. The heating element is formed in a pattern to apply heat through the band to the nozzle. The heating element has first and second ends. Each end has an electrical terminal. A second dielectric layer is directly deposited over the heating element, but not over the terminals.

U.S. Pat. No. 6,923,638 (Inventor: Chen; Published: 2005 Aug. 02) discloses a hot melt distribution manifold. The manifold includes a body and a main runner. The main runner is located in the body. The body has an inlet for receiving hot melt from a source of supply. A plurality of branches located in the body has intersections with the main runner at spaced locations along its length so that at least certain intersections are farther away from the inlet than others. A plurality of nozzle assemblies is located on the body and the nozzles communicate with the branches. Selectively-adjustable restrictor devices are associated with a plurality of the branches for adjustably constricting the space available for melt flow. The restrictor devices are located upstream from the corresponding nozzle assembly in spaced relation. Each of the restrictor devices are devoid of structure projecting from the restrictor device into the corresponding nozzle assembly.

U.S. patent application Ser. No. 2004/0130062 (Inventor: Sicilia; Published: 2004 Jul. 08) discloses a mixing device for use with a manifold in an injection molding apparatus. The mixing device includes a body having a melt channel therethrough. The melt channel has a plurality of increasing sections which have an increasing cross-sectional area in a downstream direction. A plurality of decreasing sections have a decreasing cross-sectional area in a downstream direction, and the increasing and decreasing sections alternating with each other.

U.S. patent application Ser. No. 2004/0256768A1 (Inventor: Olaru; Published: 2004 Dec. 23) discloses a stack injection molding apparatus that includes a melt homogenizing element provided between a first transfer nozzle, which is coupled to a melt source, and a second transfer nozzle, which is coupled to a manifold. The melt homogenizing element is used for redistributing a melt stream in order to provide a homogenized melt stream having a generally uniform temperature and viscosity profile or sectional distribution.

Known hot-runner balancing techniques appear to include geometric and/or thermal balancing of molding material channels leading into a mold cavity of a mold. These techniques have problems associate with them. Geometric balancing is used to maintain equal pressures across all drops of the hot runner. Flow control may be achieved in two ways by: (i) making the molding material travel a longer distance before it reaches the nozzle tip, or (ii) by opening a restriction near the nozzle tip (which would increase the flow out of the nozzle for the same inlet pressure).

SUMMARY

According to a first aspect of the present invention, there is provided a molding system having a melt pathway configured to convey a molding material, the molding system having: a viscous-drag sensor being interactable with the molding material, the viscous-drag sensor including: (i) a pathway blockage being movable along the melt pathway, the pathway blockage being movable along a first direction to further open the melt pathway, and the pathway blockage being movable along a second direction to further close the melt pathway; and (ii) an actuator being coupled with the pathway blockage, the actuator biasing the pathway blockage to vary the melt pathway while the molding material drags along and moves the pathway blockage, and responsive to the pathway blockage sensing a viscous-drag force, the pathway blockage acts to: (i) further open the melt pathway if a viscosity of the molding material is high, and (ii) further close the melt pathway if the viscosity of the molding material is low.

According to a first aspect of the present invention, there is provided a molding system, including a viscous-drag sensor interactable with a molding material flowable along a melt pathway.

According to a second aspect of the present invention, there is provided a method of a molding system, the method including interacting a viscous-drag sensor with a molding material flowable along a melt pathway.

A technical effect, amongst other technical effects, of the aspects of the present invention is improved balancing of flow of a molding material, and this effect is achieved by using the intrinsic properties of viscosity of a molding material. For example, even if a manifold of a hot-runner was thermally unbalanced, the aspects of the present invention are able to compensate for balancing, at least in part, of a thermally-unbalanced hot runner (of which the hot runner is an example of a molding system).

According to the aspects of the present invention, control or adjustment of flow of a molding material from a nozzle is achieved by using intrinsic properties of the viscosity of the molding material. A molding material having a higher viscosity creates a larger shear force as the molding material flows. Conversely, a molding material having a lower viscosity creates a smaller shear force. The shear force is directly proportional to the viscosity of the molding material (for constant velocity). Also, a highly-viscous molding material provides more resistance to flow than does a less-viscous molding material. Hence, for the same inlet pressure at each drop (assuming a geometrically-balanced hot runner), the highly-viscous molding material will flow relatively slower than the less-viscous molding material. To balance the hot runner, the difference in viscosities, and hence shear forces, are used to: (i) increase velocity, and hence flow rate, of the higher-viscosity molding material and (ii) reduce the velocity of the less-viscous molding material.

BRIEF DESCRIPTION OF THE DRAWINGS

A better understanding of the exemplary embodiments of the present invention (including alternatives and/or variations thereof) may be obtained with reference to the detailed description of the exemplary embodiments along with the following drawings, in which.

The drawings are not necessarily to scale and are sometimes illustrated by phantom lines, diagrammatic representations and fragmentary views. In certain instances, details that are not necessary for an understanding of the embodiments or that render other details difficult to perceive may have been omitted.

DETAILED DESCRIPTION OF THE EXEMPLARY EMBODIMENTS

Figure 1:
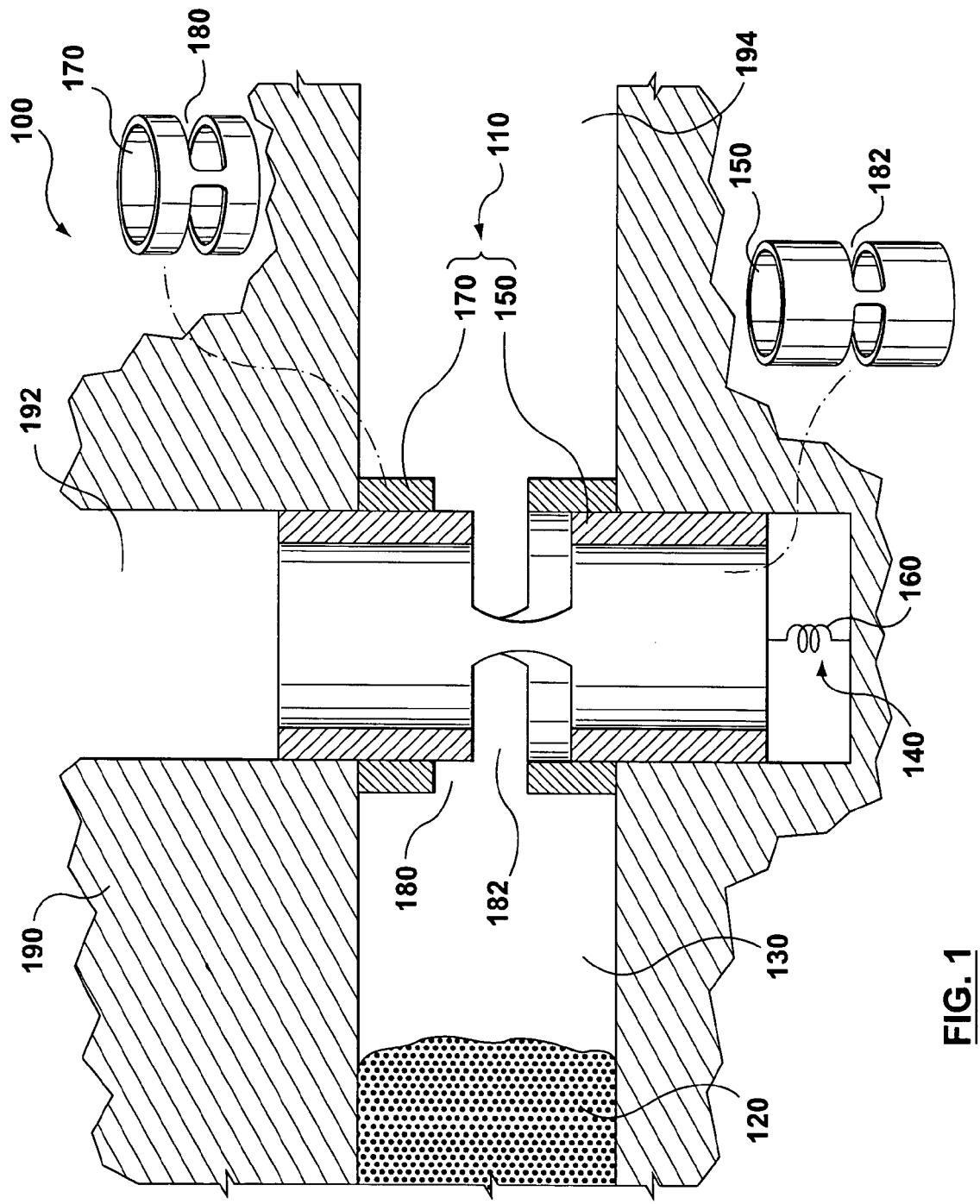
FIG. 1 is a cross sectional view of a molding system according to a first exemplary embodiment.

FIG. 1 is the cross sectional view of a molding system 100 (hereafter referred to as the "system 100") according to the first exemplary embodiment. The system 100 includes a viscous-drag sensor 110 (hereafter referred to as the "sensor 110"). The sensor 110 is interactable with a molding material 120 that is flowable along a melt pathway 130 of the system 100.

Preferably, the melt pathway 130 is defined in a hot-runner manifold 190 (which is an example of a component of the system 100). According to a variant (not depicted), the melt pathway 130 is defined in: (a) a hot sprue (not depicted) and/or (b) a machine nozzle (not depicted) which are examples of components of the system 100. The molding material 120 is made to: (i) flow along the melt pathway 130 (in the manner known to those skilled in the art) and then (ii) strike and flow past the sensor 110. The flowing molding material 120 drags along a surface or a portion of the sensor 110 and imparts a drag force to the sensor 110. Responsive to the sensor 110 sensing the drag force imparted by the molding material 120 flowing along the melt pathway 130, the sensor 110, at least in part, adjusts flow of the molding material 120. The sensor 110 is movable responsive to the sensor 110 sensing drag from the molding material 120. As the sensor 110 moves relative to the melt pathway 130, movement of the sensor 110 causes flow of the molding material 120 to vary in the following manner: (i) if the molding material 120 has a low viscosity, the sensor 110 reacts to reduce the rate of flow of the molding material 120, and/or (ii) if the molding material 120 has a high viscosity, the sensor 110 reacts to increase the rate of flow of the molding material 120.

Preferably, the sensor 110 is placed in a drop of a multi-drop hot runner (the molding system 100 is the multi-drop hot runner), and the sensor 110 is used to control flow of the molding material made to flow through a drop of the multi-drop hot runner. The sensors 110 are placed in each drop and once the molding material flows, the hot runner becomes substantially balanced (as a result of using the sensors 110). A balanced hot runner has substantially equal pressure distribution in each drop (which ensures balanced part filling and reduces risk of material damage, and improves part-to-part consistency of a molded article). The hot-runner manifold 190 is hereafter referred to as the "manifold 190". The multi-drop hot runner includes the manifold 190 that leads to multiple drops 192, 194 that in turn lead into a mold cavity defined by a mold (not depicted) that is operatively coupled to the manifold 190. In each selected drop of the manifold 190, a respective viscous-drag sensor is installed so that flow of the molding material 120 into the mold may become balanced by usage of the sensor 110. FIG. 1 depicts the sensor 110 installed in the drop 192 for simplifying the view of the sensor 110. The sensor 110 may also be installed in the drop 194 (if required, but FIG. 1 depicts the sensor 110 not installed in the drop 194). If the molding material located in the drop 192 has a high viscosity while the molding material located in the drop 194 has a low viscosity, viscous-drag sensors located in respective drops 192, 194 may react to the molding material in respective drops 192, 194 so as to either impede or promote flow of the molding material according to the viscosity of the molding material located in the respective drops 192, 194, and in this manner, flow of the molding material 120 into the mold may become balanced. The viscosity of the molding material 120 located in each drop 192, 194 may be different due to temperature fluctuations in the manifold 190, or for other reasons, etc, and this difference may be enough to cause an imbalanced flow into the mold (disadvantageously).

Preferably, the sensor 110 includes a pathway blockage 150, a hollow tube 170 and an actuator 140, such as a spring 160 for example. The actuator 140 couples the pathway blockage 150 to the manifold 190. The spring 160 biases the pathway blockage 150 to constrict the melt pathway 130. The molding material 120 drags along and moves the pathway blockage 150 in a direction to either: (i) further open the melt pathway 130 if the viscosity of the molding material 120 is high or (ii) further close the melt pathway 130 if the viscosity of the molding material 120 is low. The amount of drag sensed by the sensor 110 is a function of: the viscosity of the molding material 120, the type of material that the sensor 110 is made from and/or the type of surface finish of the sensor 110 that comes into contact with the molding material 120. The pathway blockage 150 includes a hollow tube that is receivable in the melt pathway 130 (preferably the pathway blockage 150 is receivable in the drop 192). The pathway blockage 150 also defines a portal 182. The hollow tube 170 receives the pathway blockage 150. The hollow tube 170 defines a portal 180 that is closable and openable by the pathway blockage 150. The degree to which the portal 180 and the portal 182 become aligned or misaligned permits reduced flow or increased flow of the molding material 120. Responsive to the sensor 110 sensing viscous-drag force, the actuator 140 actuatably moves the sensor 110 to adjust or amend blockage of the melt pathway 130 so that flow of the molding material 120 through the melt pathway 130 varies.

Figure 2:
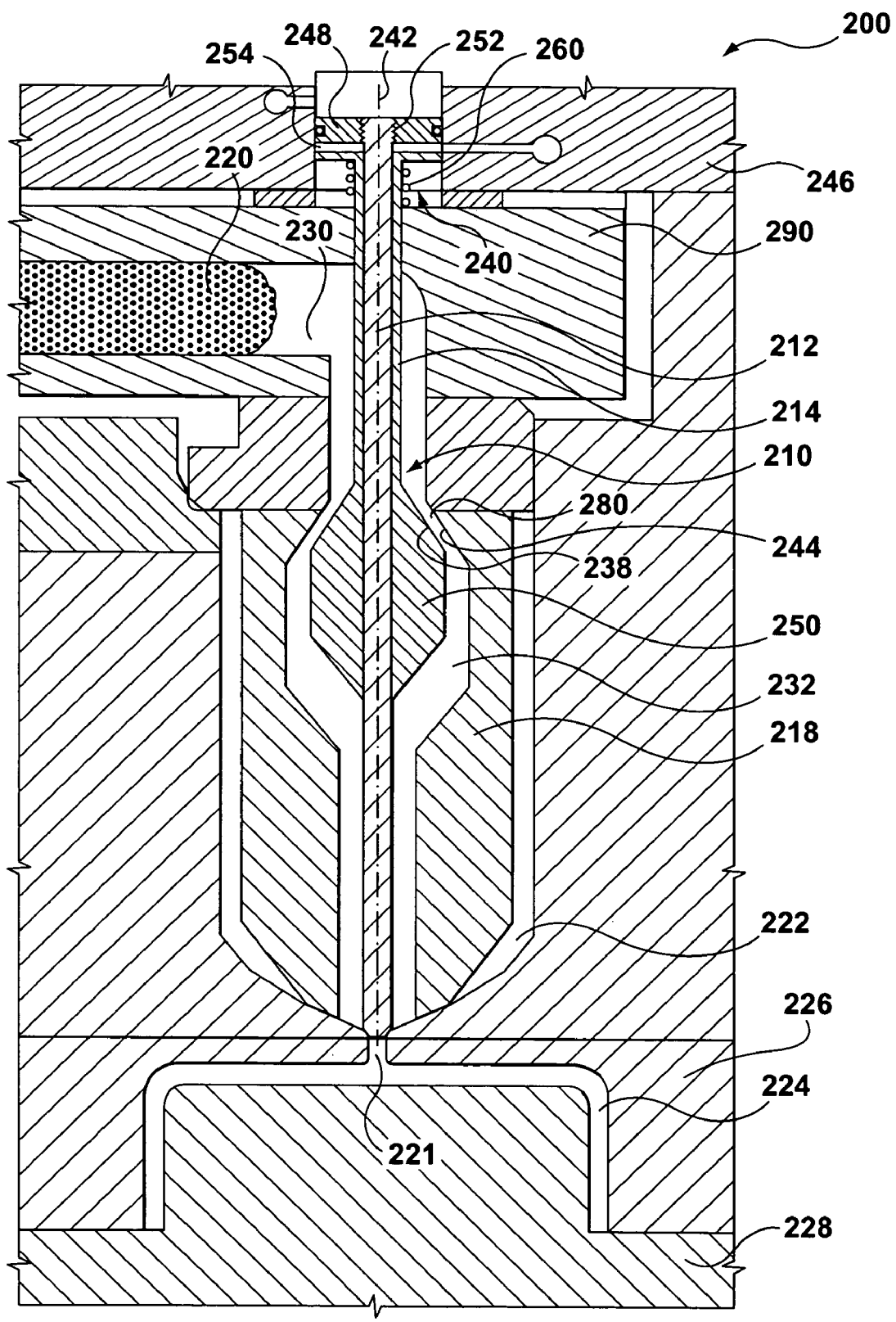
FIG. 2 is a cross sectional view of a molding system according to a second exemplary embodiment (which is the preferred embodiment)

FIG. 2 is the cross sectional view of a molding system 200 (hereafter referred to as the "system 200") according to the second exemplary embodiment. To facilitate an understanding of the second exemplary embodiment, elements of the second exemplary embodiment (that are similar to those of the first exemplary embodiment) are identified by reference numerals that use a two-hundred designation rather than a one-hundred designation (as used in the first exemplary embodiment). For example, the sensor of the second exemplary embodiment is labeled 210 rather than being labeled 110.

The system 200 is depicted as a hot-runner system (sometimes also referred to as a runner or a runner assembly or a runner sub-system) for use with an injection molding system or for use with any type of molding system. A molding material 220 is made to travel along a melt pathway 230, which is defined by the system 200 (specifically, the melt pathway 230 is defined by the manifold 290), over to a bore 232 of a nozzle 218 (the nozzle 218 is positioned in a drop 222). The molding material 220 travels along the bore 232 of the nozzle 218 and into a gate 221 and then into a mold cavity 224. The mold cavity 224 is defined by mold portions 226, 228. The manifold 290 distributes the molding material 220 to a plurality of drops, but only the drop 222 is depicted to ease description of the second exemplary embodiment. Although a hot runner system is depicted in which plastic-based melt is injected into the mold cavity 224, other types of injection systems may also use the second exemplary embodiment in which it is useful to balance the rate of flow of molding material (metal-based, plastic-based, fiber composite, etc) through multiple drops. A single gate, single cavity system is depicted. However, according to a variant, a multi-cavity system is used.

A valve pin 212 is used to control (start and stop) flow of the molding material 220 into the gate 221. A viscous-drag sensor 210 (hereafter referred to as the "sensor" 210) is used to balance flow between multiple drops (not depicted). The sensor 210 includes a body 214 and a pathway blockage 250. The body 214 and the pathway blockage 250 are integrally formed (alternatively, the pathway blockage 250 attaches to the body 214). The pathway blockage 250 is configured to be wider than the body 214 in order to restrict flow of molding material 220 in the bore 232. The body 214 and pathway blockage 250 are both of hollow construction so that the body 214 and the pathway blockage 250 receive the valve pin 212, and in this manner the valve pin 212 operates independently of the sensor 210. The sensor 210 may assume intermediate positions between a fully-open position and a fully-closed position in order to increase or decrease the rate of flow of the molding material 220 (while the valve pin 212 is displaced away from the gate 221). The pathway blockage 250 includes a tapered portion 238 that forms a gap 280 with a surface 244 of the bore 232 of the nozzle 218. The size of the gap 280 increases or decreases as the sensor 210 becomes displaced due to the sensor 210 responding to drag from the molding material 220, so that flow of molding material 220 to the gate 221 increases or decreases. Displacement of the sensor 210 is achieved when the molding material 220 flows over the body 214 and the pathway blockage 250; the molding material 220 imparts a viscous drag force to the body 214 and the pathway blockage 250. If the molding material 220 has a high-viscosity, a greater drag force is imparted to the sensor 210 and in turn, a greater displacement of the sensor 210 is achieved and gap 280 is widened. Once the gap 280 is widened, the flow rate of the molding material 220 increases through the bore 232 allowing additional molding material 220 to reach the gate 221. If the molding material 220 has a low-viscosity or is relatively thin, a smaller drag force is imparted to the sensor 210 and in turn, a smaller displacement of the sensor 210 is achieved and the gap 280 is decreased in size. Once the gap 280 is decreased in size, the flow rate of the molding material 220 decreases through the melt pathway 230 allowing less molding material 220 to reach the gate 221.

Preferably, both the valve pin 212 and the sensor 210 are displaceable independent of each other. The valve pin 212 controls when flow of molding material 220 occurs while the viscous drag sensor controls the rate of flow of the molding material 220 into the mold cavity 224. Both the valve pin 212 and the sensor 210 are controllable by independent actuation mechanisms that are placed in a single, simple location to save space and cost for fabrication. The valve pin actuator 242 is preferably mounted in a plate 246. The valve pin actuator 242 is a pneumatic actuator; however, hydraulic or electronic actuators may be used. The actuator 242 includes a pneumatic circuit That has a movable piston 248 (hereafter referred to as the "piston 248") in which the valve pin 212 is threadably mounted at a mounting position 252. According to a variant, the pneumatic circuit may be located below the piston 248 asopposed to above as depicted in FIG. 2. Thus as the piston 248 moves, the valve pin 212 moves along with the piston 248. The valve pin actuator 242 includes a space 254 which separates the piston 248 from the surface of the manifold 290. Inside the space 254, an actuator 240 is located. The actuator 240 is configured to operate in positions between the bottom of the piston 248 and the surface of the manifold 290. The actuator is 240 is preferably a spring 260. The spring 260 biases the pathway blockage 250 to constrict the gap 280. The molding material 220 drags along and moves both the body 214 and the pathway blockage 250 in a direction to either: (i) further open the gap 280 if the viscosity of the molding material 220 is high or (ii) further close the gap 280 if the viscosity of the molding material 220 is low. Responsive to the sensor 210 sensing viscous-drag force, the actuator 240 actuatably moves the sensor 210 to amend (that is, widen or narrow) the gap 280 so that flow of the molding material 220 through the melt pathway 230 varies. It is preferred that the actuator 240 is located in the space 254 since this would advantageously utilize space already available in common valve pin actuation mechanisms such as pneumatic, hydraulic or electric piston mechanisms. This utilization of the space 254 beneath the piston 248 is very advantageous in that it may be applied retroactively to hot runner systems currently in use in the industry today with limited modification of existing hot runner assemblies.

Figure 3:
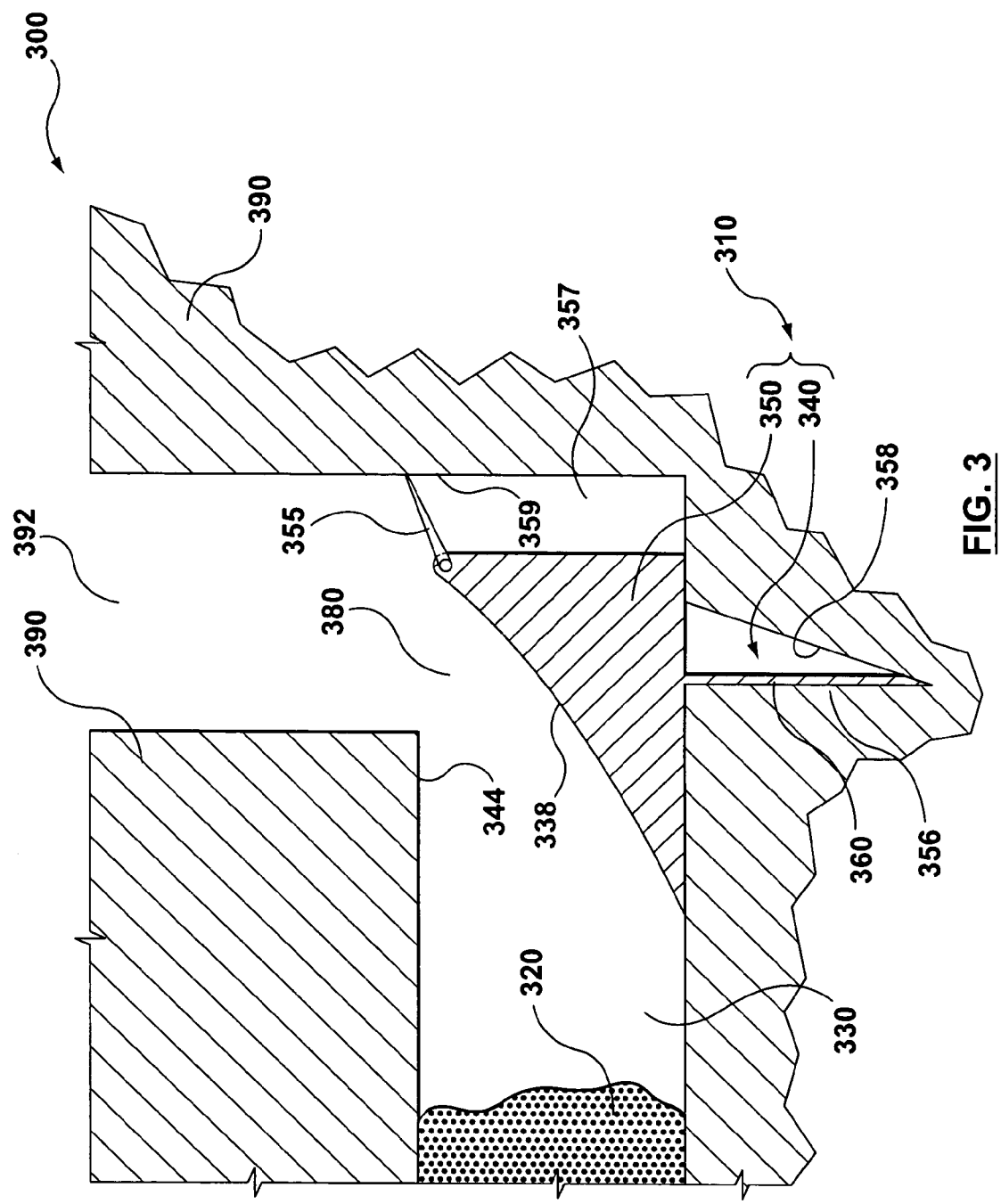
FIG. 3 is a cross sectional view of a molding system according to a third exemplary embodiment.

FIG. 3 is the cross sectional view of a molding system 300 (hereafter referred to as the "system 300") according to the third exemplary embodiment. To facilitate an understanding of the third exemplary embodiment, elements of the third exemplary embodiment (that are similar to those of the first exemplary embodiment) are identified by reference numerals that use a three-hundred designation rather than a one-hundred designation (as used in the first exemplary embodiment). For example, the sensor of the third exemplary embodiment is labeled 310 rather than being labeled 110.

A molding material 320 is made to travel along a melt pathway 330 that is defined by the system 300. Preferably, the melt pathway 330 is defined by a manifold 390. A viscous-drag sensor 310 (hereafter referred to as the "sensor 310") is positionable in the melt pathway 330. The sensor 310 includes a pathway blockage 350 and an actuator 340 that is attached to a back side of the pathway blockage 350 (hereafter referred to as the "blockage" 350). The back side of the pathway blockage 350 is abutable against and is slidable along an inner wall of the melt pathway 330. A front side of the pathway blockage 350 faces the molding material 320. The actuator 340 is preferably a leaf spring 360. The leaf spring 360 is received into a recess or a hole defined in the manifold 390 and the recess extends from the inner wall of the melt pathway 330 into the interior of the manifold 390. The pathway blockage 350 includes a tapered portion 338 (which may also be called a wedge). A gap 380 if formed between the tapered portion 338 and a surface 344 of the melt pathway 330 (the surface 344 is located opposite of the tapered portion 338). The surface 344 forms a corner section of the melt pathway 330. The size of the gap 380 increases or decreases as the sensor 310 is displaced (that is, slides along the melt pathway 330) due to the sensor 310 responding to drag from the molding material 320. Displacement (or movement) of the sensor 310 is achieved when the molding material 320 flows aver the tapered portion 338 and then drags the sensor 310 along. In this manner, the molding material 320 imparts a viscous drag force to the tapered portion 338. If the molding material 320 has a high-viscosity, a greater drag force is imparted on the tapered portion 338 and in turn, a greater displacement of the sensor 310 is achieved and as a result, the gap 380 is widened. Once the gap 380 is widened, the flow rate of the molding material 320 increases through the melt pathway 330. If the molding material 320 has a low-viscosity or is relatively thin, a smaller drag force is imparted to the sensor 310 and in turn, a smaller displacement of the sensor 310 is achieved and the gap 380 is decreased in size. Once the gap 380 is decreased in size, the flow rate of the molding material 320 decreases through the melt pathway.

The actuator 340 is configured to operate in positions between a first manifold wall 356 and a second manifold wall 358 (the walls 356, 358 define the recess in which the leaf spring 360 resides); the two manifold walls 356, 358 preferably define an acute angle between themselves. The leaf spring 360 is attached to the location where the two walls 356, 358 meet The leaf spring 360 biases the pathway blockage 350 to move toward wall 356 and away from wall 358. The molding material 320 moves and drags along the pathway blockage 350 in a direction to either: (i) further open (or widen) the gap 380 if the viscosity of the molding material 320 is high or (ii) further close (or narrow) the gap 380 if the viscosity of the molding material 320 is low. Responsive to the sensor 310 sensing viscous-drag force, the leaf spring 360 actuatably moves the sensor 310 to amend the gap 380 so that flow of the molding material 320 through the melt pathway 330 may vary.

According to a variant, the sensor 310 also includes a flow-check arm 355 pivotably attached to the pathway blockage 350. The flow-check arm 355 is configured to continuously abut a pathway wall 359 in order to prevent molding material 320 flowing over the tapered portion 338 (and to the rearward portion of the pathway blockage 350) from seeping behind the pathway blockage 350 and collecting in a crevice 357.

Figure 4:
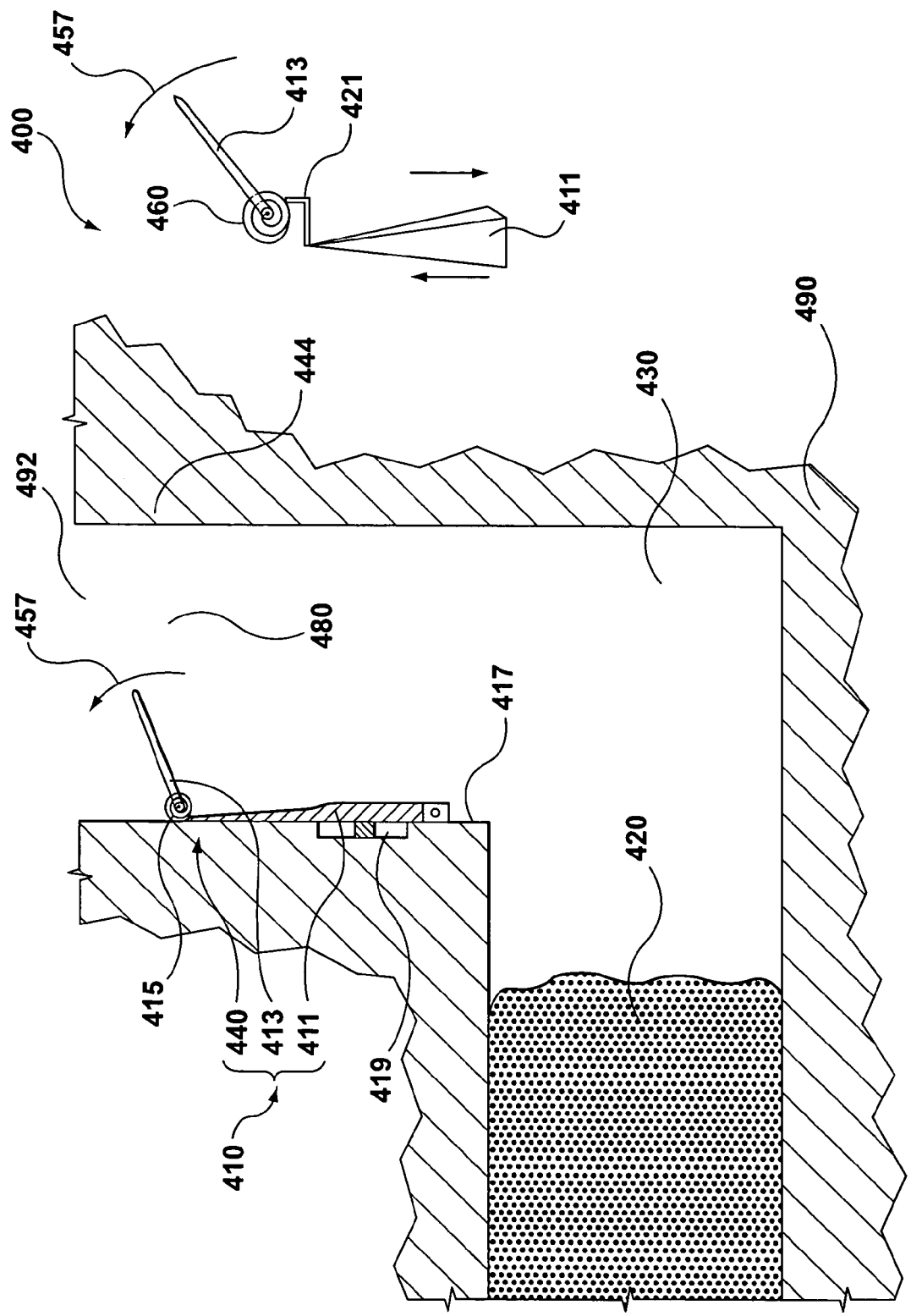
FIG. 4 is a cross sectional view of a molding system according to a fourth exemplary embodiment.

FIG. 4 is a cross sectional view of a molding system 400 (hereafter referred to as the "system 400") according to the fourth exemplary embodiment. To facilitate an understanding of the fourth exemplary embodiment, elements of the fourth exemplary embodiment (that are similar to those of the first exemplary embodiment) are identified by reference numerals that use a four-hundred designation rather than a one-hundred designation (as used in the first exemplary embodiment). For example, the sensor of the third exemplary embodiment is labeled 410 rather than being labeled 110.

A viscous-drag sensor 410 (hereafter referred to as the "sensor 410") is interactable with a molding material 420 that is flowable along a melt pathway 430 of the system 400, past a gate 492 that leads into a mold cavity of a mold (not depicted). The sensor 410 includes a passageway blockage 450 and an arm 413 that is rotatably spring biased relative to the passageway blockage 450 at a biasing point 415. The biasing point 415 is located on an end of the passageway blockage 450. The sensor 410 is positioned along a wall 417 of the melt pathway 430. The arm 413 is used to control (adjust) flow of the molding material 420. The passageway blockage 450 is flat, is abutable against the wall 417 and is slidably retained along the wall 417 so that the passageway blockage 450 may reciprocate. A groove 419 is defined in the wall 417 and the groove 419 is used to limit sliding of the passageway blockage 450 between a high-flow position and a low-flow position, and to retain the passageway blockage 450 adjacent to the wall 417 at all times of operation. The arm 413 extends from the biasing point 415 and into the melt pathway 430 so as to facilitate flow control of the molding material 420. A gap 480 is defined between an end of the arm 413 (that is, the end opposite from the biasing point 415) and a surface 444 of a manifold 490 of the system 400. The size of the gap 480 increases or decreases as the arm 413 is made to rotate as a result of the sensor 410 responding to drag from the molding material 420. Flow control of the molding material 420 is achieved as follows: (i) if the molding material 420 has a high viscosity (and is made to flow over the passageway blockage 450), the molding material 420 imparts a viscous drag force to the passageway blockage 450 and in turn the passageway blockage 450 is made to translate sufficiently enough so as to rotate the arm 413 (and store energy in an actuator 440, which is a spring-biasing mechanism). The method of rotation of the arm 413 is described below. Once the arm 413 rotates, the gap 480 is widened. Once the gap 480 is widened, the flow rate of the molding material 420 increases, and (ii) if the molding material 420 has a low viscosity or is relatively thin, a smaller drag force is imparted to the passageway blockage 450 and in turn the actuator 440 (that couples the arm 413 to the passageway blockage 450) urges the passageway blockage 450 to slide away from the arm 413 and the gap 480 is decreased in size. Once the gap 480 is decreased in size, the flow rate of the molding material 420 decreases through the melt pathway 430.

The actuator 440 (hereafter referred to as the "actuator" 440). The actuator 440 couples (spring biases) the passageway blockage 450 to the arm 413 at the biasing point 415. The actuator 440 is configured to operate in relation to the passageway blockage 450 sliding due to the viscous drag force imparted by the molding material 420. The actuator 440 is preferably a torsional spring 460. Responsive to the passageway blockage 450 sliding, the torsional spring 460 receives an input torque. The input torque exerted on the torsional spring 460 is achieved via a linkage 421 that links the passageway blockage 450 to the torsional spring 460. One side of the linkage 421 is attached to the passageway blockage 450 while the other side is attached to the torsional spring 460. As the passageway blockage 450 slides due to the viscous drag force imparted to the passageway blockage 450 by the molding material 420, the linkage 421 slides along with the passageway blockage 450. The sliding of linkage 421 is opposed by the torsional spring 460 which is rigidly connected to the biasing point 415 and not allowed to rotate freely (the biasing point 415 is located at an end of the arm 413). The opposition of sliding in turn produces a torque on the torsional spring 460. The only torque exerted on the torsional spring 460 prior to the linkage 421 exerting the input torque is the molding-material-flow torque 457 caused by the molding material 420 flowing past the arm 413 (which is rigidly attached to the torsional spring 460 at the coupling point) and inducing a force on the arm 413 and in turn inducing a torque on the torsional spring 460. Since: (i) a greater net torque is placed on the torsional spring 460 due to both the linkage 421 and (ii) the molding material 420 and the torsional spring 460 is not able to withstand a greater net torque without rotating, a rotation of the torsional spring 460 and the arm 413 will result. The rotation of arm 413 increases the size of gap 480, allowing more molding material 420 to travel to the gate 492. If the molding material 420 has a low viscosity, then the viscous drag force would not be as great on the passageway blockage 450. The lack of force (that is force imparted to the passageway blockage 450) due to a lower viscosity of the molding material 120 will result in the passageway blockage 450 sliding back to its starting, or low-flow position due to the torsional spring exerting a stored torque to the linkage 421 and in turn causing the linkage 421 and the passageway blockage 450 to slide back. The lack of viscous-drag force would cause the net torque to decrease and in turn cause the arm 413 to rotate to constrict the gap 480 and allow less molding material 420 to flow through The melt pathway 430 to the gate 492. The torsional spring 460 spring biases the arm 413 to constrict the gap 480. The molding material 420 drags along and moves the passageway blockage 450 in a direction to either: (i) further open the gap 480 if the viscosity of the molding material 420 is high or (ii) further close the gap 480 if the viscosity of the molding material 420 is low. Responsive to the sensor 410 sensing viscous-drag force, the torsional spring 460 actuatably rotates the arm 413 to amend (that is, widen or narrow) the gap 480 so that flow of the molding material 420 through the melt pathway 430 varies.

Figure 5:
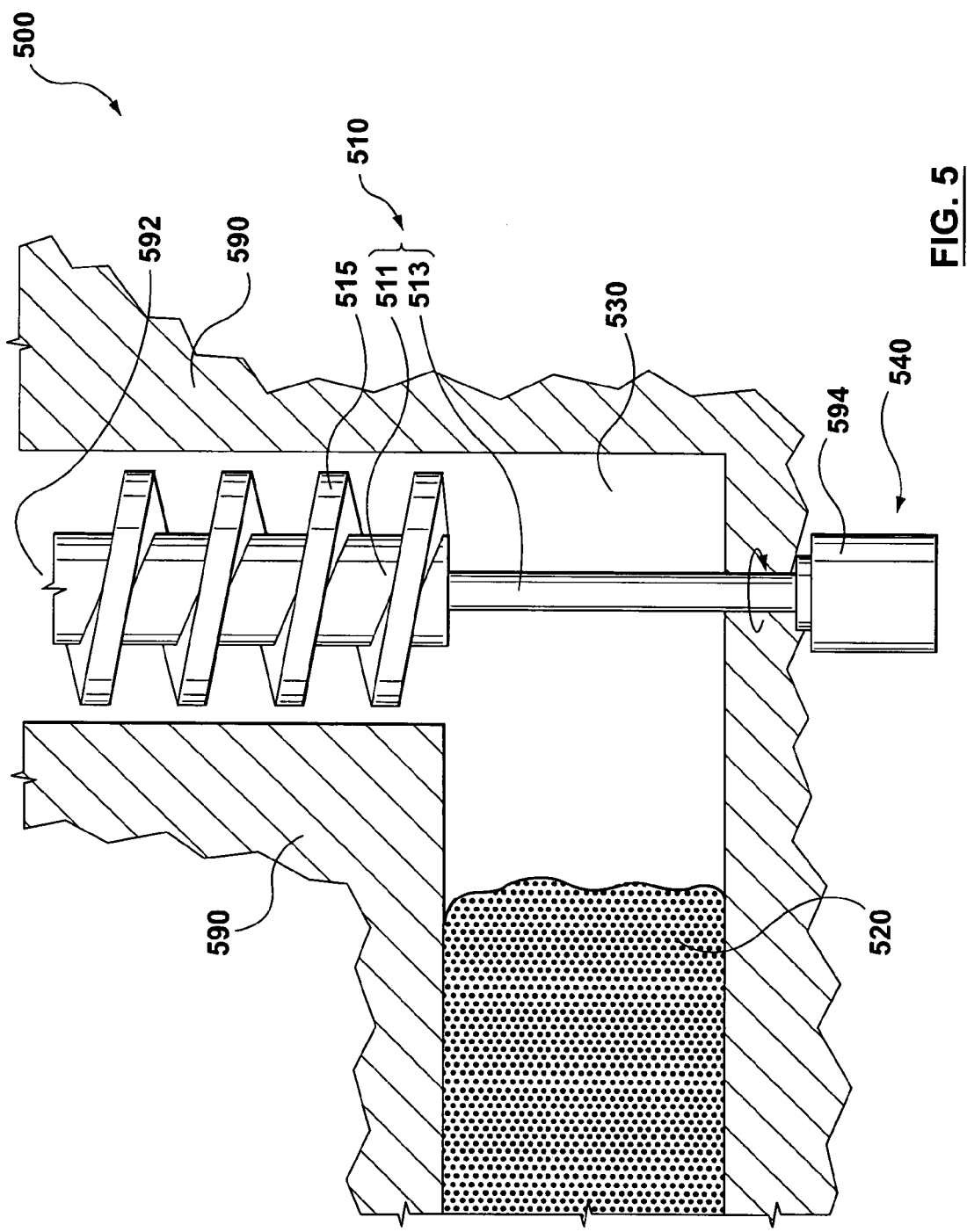
FIG. 5 is a cross sectional view of a molding system according to a fifth exemplary embodiment.

FIG. 5 is a cross sectional view of a molding system 500 (hereafter referred to as the "system 500") according to the fifth exemplary embodiment. To facilitate an understanding of the fifth exemplary embodiment, elements of the fifth exemplary embodiment (that are similar to those of the first exemplary embodiment) are identified by reference numerals that use a five-hundred designation rather than a one-hundred designation (as used in the first exemplary embodiment). For example, the sensor of the fifth exemplary embodiment is labeled 510 rather than being labeled 110. A viscous-drag sensor 510 (hereafter referred to as the "sensor 510") is interactable with a molding material 520 that is flowable along a melt pathway 530 of the system 500. The sensor 510 includes a screw 511 and a shaft 513 that is connectable or couplable to the screw 511. The shaft 513 and the screw 511 are axially parallel once connected together. The sensor 510 is positioned in the melt pathway 530. The melt pathway 530 extends through a manifold 590 and ends or terminates at a gate 592 that leads into a mold (not depicted). The location of the sensor 510 in the melt pathway 530 is such that flow characteristics (of the molding material 520) are adjustable prior to the molding material 520 reaching the gate 592. The screw 511 is cylindrical and has a set of helical flights 515 winding along a longitudinal axis of the screw 511. Preferably, the screw 511 has a constant pitch and a constant diameter. According to a variant, the screw 511 has a non-constant pitch; according to another variant, The screw 511 has a variable pitch and a variable diameter. The flight diameter of the set of helical flights 515 is preferably smaller than the diameter of the melt pathway 530 (but reaching close to the side walls of the melt pathway 530). This way, the molding material 520 is made to flow and interact with the sensor 510 and does not (preferably) substantially bypass the sensor 510. An actuator 540 is coupled to the shaft 513. The actuator 540 is used to rotate (clockwise, for example) the shaft 513 and the screw 511 with a constant torque.

As molding material 520 is made to flow along the melt pathway 530 toward the gate 592, the molding material 520 encounters the screw 511 and flows along the set of helical flights 515 in order to travel past the screw 511 and then enter the gate 592. In doing so, the molding material 520 exerts a viscous-drag force to the set of helical flights 515. The viscous drag force imparted to the screw 511 causes the screw 511 to rotate (counter clockwise, for example).

The sensor 510 senses the drag force and counters the drag force by adjusting the relative rate of rotation of the sensor 510 with the manifold 590. The screw 511 and the shaft 513 rotate at a constant torque in an opposing direction of the flow rotation of the molding material 520. The actuator 540 creates: (i) a faster counter rotation to flow direction once a low-viscosity molding material 520 passes over the sensor 510, and (ii) a slower counter rotation to flow direction once a high-viscosity molding material 520 passes over the sensor 510.

The actuator 540 is mounted in the manifold 590. The actuator 540 is preferably a constant torque electric motor 594 (hereafter referred to as the "motor 594"); according to a variant, the motor 594 includes a hydraulic or a pneumatic motor. The motor 594 is used to rotate the shaft 513 and rotation of the shaft 513 causes further rotation of the screw 511 (which is rigidly attached or coupled to the shaft 513). The motor 594 rotation direction is in the opposite direction of the rotation induced on the screw 511 by the viscous drag force. As the molding material 520 flows past the set of helical flights 515, the molding material 520 imparts a viscous drag force to the screw 511 creating a rotation in the flow direction of the molding material. Responsive to the screw 511 rotating due to the viscous drag force imparted to the screw 511 by the molding material 520, the motor 594 creates an opposite direction of rotation in order to counter the flow of the molding material 520. The motor 594 creates rotation at a constant torque so as to vary speed of rotation with different drag conditions. If a high viscosity molding material 520 flows past the screw 511, (i) a high viscous drag force will be imparted on the screw 511 and (ii) the motor 594 will rotate at a constant torque but slower speed due to the high viscous drag force resulting in a higher flow rate of molding material 520 past the screw 511. If a low viscosity molding material 520 flows past the screw 511, (i) a low viscous drag force will be imparted on the screw 511 and (ii) the motor 594 will rotate at a constant torque but higher speed due to the low viscous drag force resulting in a lower flow rate of molding material 520 past the screw 511. Responsive to the sensor 510 sensing viscous-drag force, the motor 594 actuatably rotates the screw 511 to amend (that is, increase or decrease) the molding material 520 flow rate so that flow of the molding material 520 through the melt pathway 530 varies. The sensor 510 creates a self-priming system, causing heterogeneous (at least in part) molding material (in terms of viscosity) to flow at similar rates from each drop of the molding system and this provides and improved balancing of the molding system.

Figure 6:
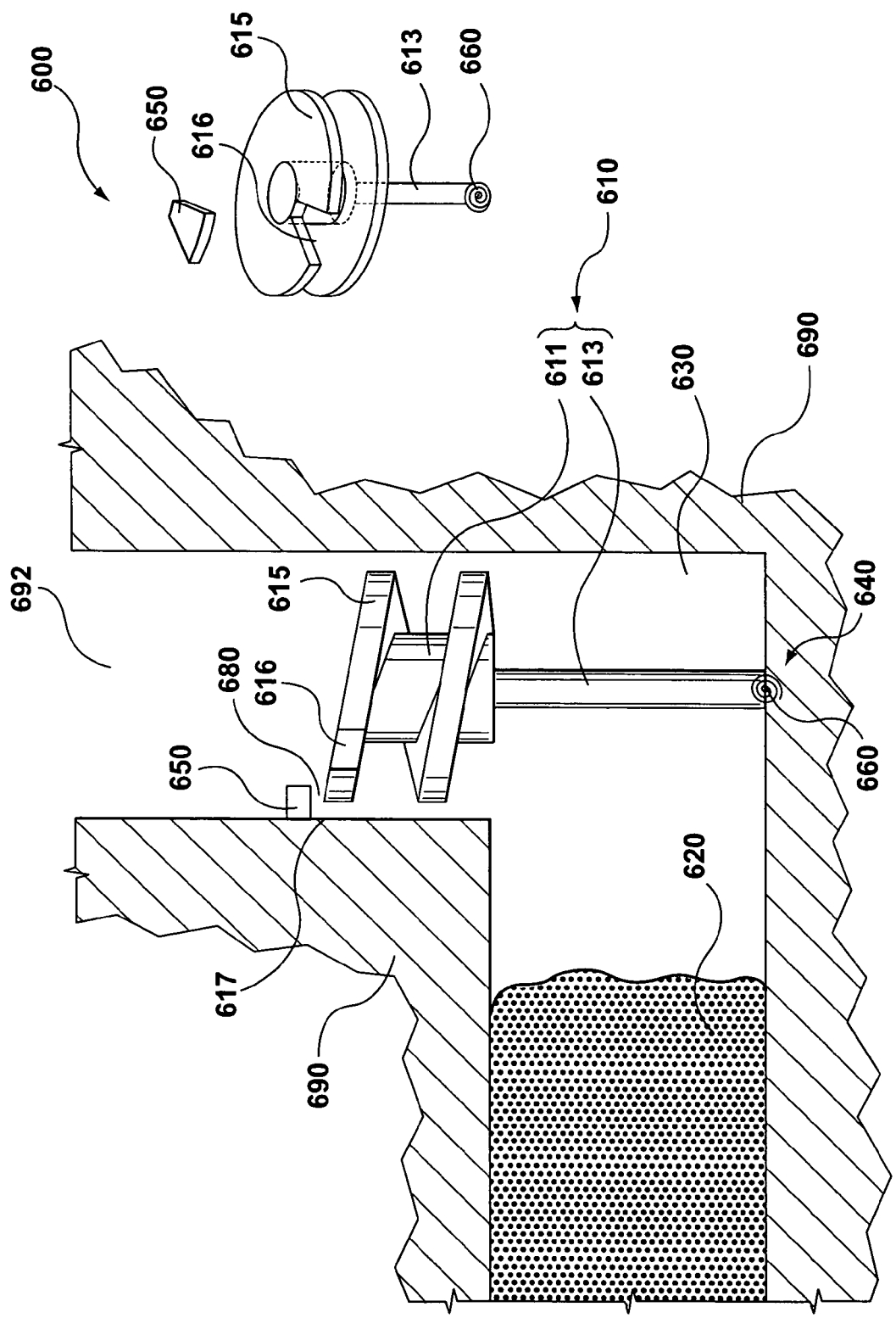
FIG. 6 is a cross sectional view of a molding system according to a sixth exemplary embodiment.

FIG. 6 is a cross sectional view of a molding system 600 (hereafter referred to as the "system 600") according to the sixth exemplary embodiment. To facilitate an understanding of the sixth exemplary embodiment, elements of the sixth exemplary embodiment (that are similar to those of the first exemplary embodiment) are identified by reference numerals that use a six-hundred designation rather than a one-hundred designation (as used in the first exemplary embodiment). For example, the sensor of the sixth exemplary embodiment is labeled 610 rather than being labeled 110. A viscous-drag sensor 610 (hereafter referred to as the "sensor 610") is interactable with a molding material 620 that is flowable along a melt pathway 630 of the system 600. The sensor 610 is positioned in the melt pathway 630. The melt pathway 630 extends through a manifold 690 and ends at a gate 692 that leads into a mold cavity defined by a mold (not depicted). The location of the sensor 610 in the melt pathway 630 is such that flow characteristics (of the molding material 620) are adjustable or controllable prior to the molding material 620 reaching the gate 692.

Preferably, the sensor 610 includes a screw 611 and a shaft 613 that is connected or coupled to the screw 611. The shaft 613 and the screw 611 are axially aligned with each other once they are connected together. The screw 611 is cylindrical and has a set of helical flights 615 winding along a longitudinal axis extending through the screw 611. Preferably, the screw 611 has a constant pitch and a constant diameter. According to a variant, the screw 611 has a non-constant pitch; according to another variant, the screw 611 has a variable pitch and a variable diameter. The flight diameter of the set of helical flights 615 is preferably smaller than the diameter of the melt pathway 630 (but reaching close to the side walls of the melt pathway 630). In this manner, the molding material 620 is made to flow and interact with the sensor 610 and does not (preferably) substantially bypass the sensor 610. The last flight of screw 611 (located closest to the gate 692) is configured to define an exit 616 for permitting the molding material 620 to travel therethrough. Adjacent to the exit 616 of the screw 611 (located on a manifold wall 617) is a pathway blockage 650. The pathway blockage 650 is rigidly attached to (and extending from) the manifold wall 617. The pathway blockage 650 is offset from the screw 611 and is positioned so as to be in-line with the exit 616 (once the set of helical flights 615 is rotated just so). A gap 680 is defined between the pathway blockage 650 and the exit 616. The gap 680 is configured to provide a path for molding material 620 to pass therethrough on the way to the gate 692. The size of the gap 680 increases or decreases as the sensor 610 becomes rotated due to the sensor 610 responding to drag imparted to the sensor 610 from the molding material 620 so that flow of molding material 620 to the gate 692 may increase or decrease. Rotational displacement of the sensor 610 is achieved when the molding material 620 flows over the set of helical flights 615 and then imparts a viscous drag force to the set of helical flights 615 of the screw 611. If the molding material 620 has a high-viscosity, a greater drag force is imparted to the sensor 610 and in turn a greater radial displacement of the sensor 610 is achieved so that the gap 680 is widened due to misalignment of the pathway blockage 650 elative to the exit 616. Once the gap 680 is widened, the flow rate of the molding material 620 increases through the screw 611 allowing additional (or more) molding material 620 to reach the gate 692. If the molding material 620 has a low-viscosity or is relatively thin, a smaller drag force is imparted to the sensor 610 and in turn a smaller displacement of the sensor 610 is achieved so that the gap 680 is decreased in size due to close alignment of the pathway blockage 650 with the exit 616 (so as to increase blocking of the exit 616). Once the gap 680 is decreased in size, the flow rate of the molding material 620 decreases through the melt pathway 630 allowing less molding material 620 to reach the gate 621.

An actuator 640 is coupled to the shaft 613. The actuator 640 is used to bias rotation (clockwise, for example) of the shaft 613 and the screw 611 in order to control alignment of the pathway blockage 650 relative to the exit 616 (the size of the gap 680). The actuator 640 is mounted to a side wall of the melt pathway 630 of the manifold 690. The actuator 640 is preferably a torsional spring 660 (hereafter referred to as the "spring 660"). The spring 660 is used to bias rotational movement of the shaft 613 and of the screw 611. The spring 660 biases the exit 616 of the screw 611 to align with the pathway blockage 650. The spring 660 biasing direction is in the opposite direction of rotational displacement induced on the screw 611 by the viscous drag force. As the molding material 620 flows past the set of helical flights 615, the molding material 620 imparts a viscous drag force to the screw 611 thus creating misalignment of the pathway blockage 650 with the exit 616 and thus creating a larger size of the cap 680. Responsive to the screw 611 rotating due to the viscous drag force imparted to the screw 611 by the molding material 620, the spring 660 stores potential energy and creates a biasing force in the opposite direction of rotation in order to reduce the rotational displacement (misalignment) created by the viscous drag force and to control the size of gap 680. The spring 660 creates different rotational forces so as to vary the size of the gap 680 with different drag conditions. If a high-viscosity molding material 620 flows past the screw 611, (i) a high viscous drag force will be imparted to the screw 611 and (ii) the spring 660 will store more potential energy, and the spring 660 biases the rotational displacement (misalignment) of the screw 611 by a smaller amount which results in a larger size of the gap 680 and a higher flow rate of molding material 620 past the screw 611. If a low-viscosity molding material 620 flows past the screw 611, (i) a low viscous drag force will be imparted on the screw 611 and (ii) the spring 660 will store less potential energy, and the spring 660 biases the rotational displacement (misalignment) of the screw 611 by a larger amount which results in a smaller size of the gap 680 and a lower flow rate of molding material 620 past the screw 611. Responsive to the sensor 610 sensing viscous-drag force, the spring 660 actuatably rotates the screw 611 to amend (that is, increase or decrease) the size of the gap 680 so that flow of the molding material 620 through the melt pathway 630 varies.

Figure 7:
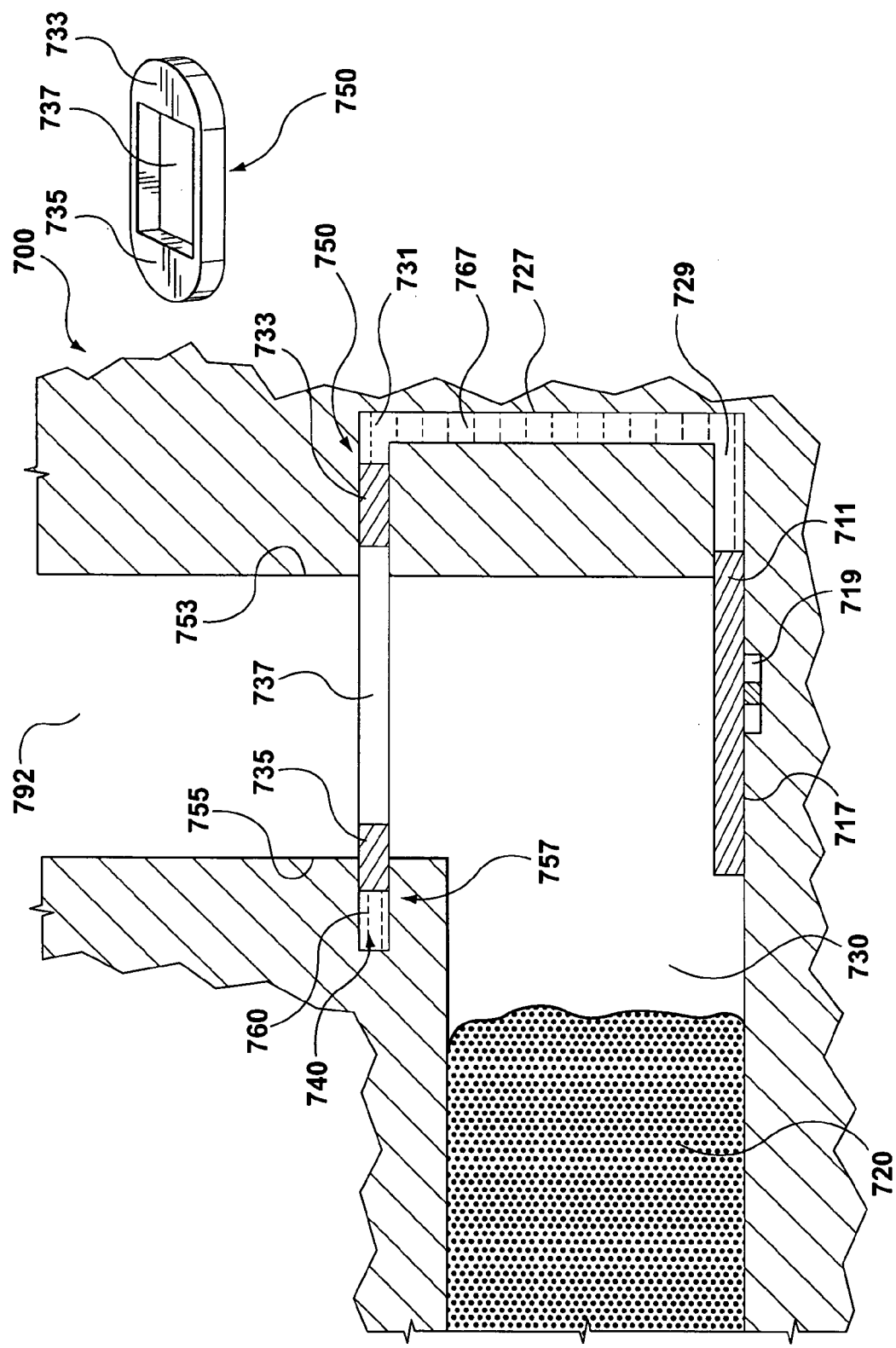
FIG. 7 is a cross sectional view of a molding system according to a seventh exemplary embodiment.

FIG. 7 is a cross sectional view of a molding system 700 (hereafter referred to as the "system 700") according to the seventh exemplary embodiment. To facilitate an understanding of the seventh exemplary embodiment, elements of the seventh exemplary embodiment (that are similar to those of the first exemplary embodiment) are identified by reference numerals that use a seven-hundred designation rather than a one-hundred designation (as used in the first exemplary embodiment). For example, the sensor of the seventh exemplary embodiment is labeled 710 rather than being labeled 110. A viscous-drag sensor 710 (hereafter referred to as the "sensor 710") is interactable with a molding material 720 that is flowable along a melt pathway 730 of the system 700. The sensor 710 is positioned in the melt pathway 730. The melt pathway 730 extends through a manifold 790 and ends at a gate 792 that leads into a mold cavity defined by a mold (not depicted). The location of the sensor 710 in the melt pathway 730 is such that flow characteristics (of the molding material 720) are adjustable or controllable prior to the molding material 720 reaching the gate 792.

Preferably, the sensor 710 includes: (i)-a pathway blockage 750 including a body 711 that is separate from the pathway blockage 750, and (ii) a fluid channel 727 configured to receive the body 711 and to receive the pathway blockage 750. The body 711 is configured to be flat and to be abutable against a bottom-manifold wall 717 of the melt pathway 730. The body 711 is slidably retained along the bottom-manifold wall 717 so that the body 711 may reciprocate within the fluid channel 727. A groove (or recess) 719 is defined in the bottom-manifold wall 717. The groove 719 is used to limit sliding of the body 711 between a high-flow position and a low-flow position. The fluid channel 727 has: (i) a first-channel end 729 from which the body 711 enters (beginning in the melt pathway 730 at a first location adjacent to the bottom manifold wall 717), and (ii) a second-channel end 731 ending in the melt pathway 730 at a second location offset from the first location. The second location is downstream and closer to the gate 792 than the first location. Defined between the two channel ends 729, 731 is a fluid channel 727 extending through the manifold 790 (preferably extending adjacent to the melt pathway 730). A portion of the body 711 is configured to retainably slide inside the first channel end 729 of the fluid channel 727. The portion of the body 711 that is not inside the first channel end 729 protrudes out of the fluid channel 727 and extends into the melt pathway 730 where it is interactable with the molding material 720 passing through the melt pathway 730.

The pathway blockage 750 is configured to have a first side 733 and a second side 735 that is offset from the first side. The melt pathway 730 defines a passage 737 between the sides 733, 735. The molding material 720 travels through the passage 737. The pathway blockage 750 is slidably positionable inside the second channel end 731 of the fluid channel 727. The first side 733 of the pathway blockage 750 is slidably retained (at least in part) within the second channel end 731. The pathway blockage 750 is preferably perpendicular in orientation relative to the flow of the melt pathway 730. The second channel end 731 ends at a first manifold wall 753 and the first manifold wall 753 defines a portion of the melt pathway 730. On the opposite side of the first manifold wall 753 is a second manifold wall 755 defining another portion of the melt pathway 730. The second manifold wall 755 contains a bore 757 configured to be: (i) preferably extending perpendicularly relative to the melt pathway 730 and into the manifold 790 and (ii) in alignment with the second channel end 731. The bore 757 houses: (i) an actuator 740 and (ii) the second side 735 of the pathway blockage 750. The actuator 740 is configured to act on the second side 735 in the bore 757 (at a location inside the manifold 790), whereas the second side 735 of the pathway blockage 750 is: (i) slidably retained within the bore 757 (at least in part), and (iii) configured to extend into the melt pathway 730. The pathway blockage 750 is slidably retained between walls of the melt pathway by having: (i) the first side 733 retained by the second channel end 731 located on the first manifold wall 753 and (ii) the second side 735 retained by the bore 757 located on the second manifold wall 755. The passage 737 is configured to be substantially parallel with the melt pathway 730 in which the passage 737 provides a path for the molding material 720 to pass therethrough on the way to the gate 792. Since the two sides 733, 735 of the pathway blockage 750 are slidably retained by channels in the manifold 790, the passage 737 is allowed to align or misalign with the melt pathway 730 depending on the position of the pathway blockage 750. The outline of the passage 737 is preferably rectangular, the size of the rectangle is preferably equal to that of the melt pathway 730 in order to allow melt flow therethrough upon perfect alignment with the melt pathway 730. According to a variant, the passage 737 is square shaped; according to another variant the passage 737 is circular shaped.

The fluid channel 727 preferably contains an incompressible fluid 767 (hereafter referred to as the "fluid 767") such as a hydraulic fluid for example. The incompressible fluid 767 is used to establish fluid communication between the body 711 and the first side 733 of the pathway blockage 750. According to a variant, the fluid 767 is a compressible fluid. The fluid 767 allows for a force to be transmitted between the body 711 and the pathway blockage 750. The size of the passage 737 increases or decreases as the sensor 710 becomes translated due to the body 711 responding to drag imparted to the body 711 from the molding material 720 so that flow of molding material 720 to the gate 792 may be controlled (increased, decreased, etc). Translational displacement of the sensor 710 is achieved when the molding material 720 flows over the body 711 and then imparts a viscous drag force to the body 711. The viscous drag force is transmitted from the body 711, through the incompressible fluid 767 and to the pathway blockage 750, creating translational motion of the sensor 710. If the molding material 720 has a high viscosity, a greater drag force is imparted to the sensor 710 and in turn a greater translational displacement of the sensor 710 is achieved so that the passage 737 is widened due to close alignment of the pathway blockage 750 relative to the melt pathway 730. Once the passage 737 is widened, the flow rate of the molding material 720 increases through the pathway blockage 750 allowing additional molding material 720 to reach the gate 792. If the molding material 720 has a low viscosity or is relatively thin, a smaller drag force is imparted to the sensor 710 and in turn a smaller displacement of the sensor 710 is achieved so that the passage 737 is decreased in size due to misalignment of the pathway blockage 750 with the melt pathway 730 (so as to increase blocking of the passage 737). Once the passage 737 is decreased in size, the flow rate of the molding material 720 decreases through the melt pathway 730 allowing less molding material 720 to reach the gate 792.

The actuator 740 is coupled to (or acts on) the second side 735 of pathway blockage 750. The actuator 740 is used to bias translational motion (toward the left side of FIG. 7, for example) of the pathway blockage 750 and the body 711 in order to control alignment of the pathway blockage 750 relative to the melt pathway 730. The alignment of pathway blockage 750 relative to the melt pathway 730 defines or controls the size of the passage 737. The actuator 740 is mounted in the bore 757 of the manifold 790. The actuator 740 is preferably a compressible gas 760 (hereafter referred to as the "gas 760"). According to a variant, a fluid is used in place of the gas 760. The gas 760 is used to bias translational movement of the pathway blockage 750 and the body 711. The gas 760 biases the passage 737 of the pathway blockage 750 to misalign with the melt pathway 730. The gas 760 biasing direction is in the opposite direction of translational displacement induced on the pathway blockage 750 and body 711 by the viscous drag force. As the molding material 720 flows past the body 711, the molding material 720 imparts a viscous drag force to the body 711. The viscous drag force slidably translates the body 711 further into the fluid channel 727 producing a force on the fluid 767. This force is then further translated from the first channel end 729, down the fluid 767 and to the second channel end 731 where a hydraulic force is then it transmitted to the pathway blockage 750, thus creating closer alignment of the pathway blockage 750 with the melt pathway 730 and thus creating a larger passage 737. Responsive to the pathway blockage 750 translating due to the viscous drag force imparted to the pathway blockage 750 by the molding material 720, the gas 760 stores potential energy and creates a biasing force in the opposite direction of translation in order to reduce the translational displacement (misalignment) created by the viscous drag force and to control the size of passage 737. The gas 760 creates different translational forces so as to vary the alignment of the pathway blockage 750 and in turn vary the size of the passage 737 with different drag conditions. If a high-viscosity molding material 720 flows past the body 711, (i) a high viscous drag force will be imparted to the body 711 and (ii) the gas 760 will store more potential energy, and the gas 760 biases the translational displacement (misalignment) of the pathway blockage 750 by a smaller amount which results in a larger passage 737 and a higher flow rate of molding material 720 past the pathway blockage 750. If a low-viscosity molding material 720 flows past the body 711, (i) a low viscous drag force will be imparted on the body 711 and (ii) the gas 760 will store less potential energy, and the gas 760 biases the translational displacement (misalignment) of the pathway blockage 750 by a larger amount which results in a smaller passage 737 and a lower flow rate of molding material 720 past the pathway blockage 750. Responsive to the sensor 710 sensing viscous-drag force, the gas 760 actuatably translates the pathway blockage 750 to amend (that is, increase or decrease) the alignment of the pathway blockage 750 with the melt pathway 730 so that flow of the molding material 720 through the passage 737 and melt pathway 730 varies.

Figure 8:
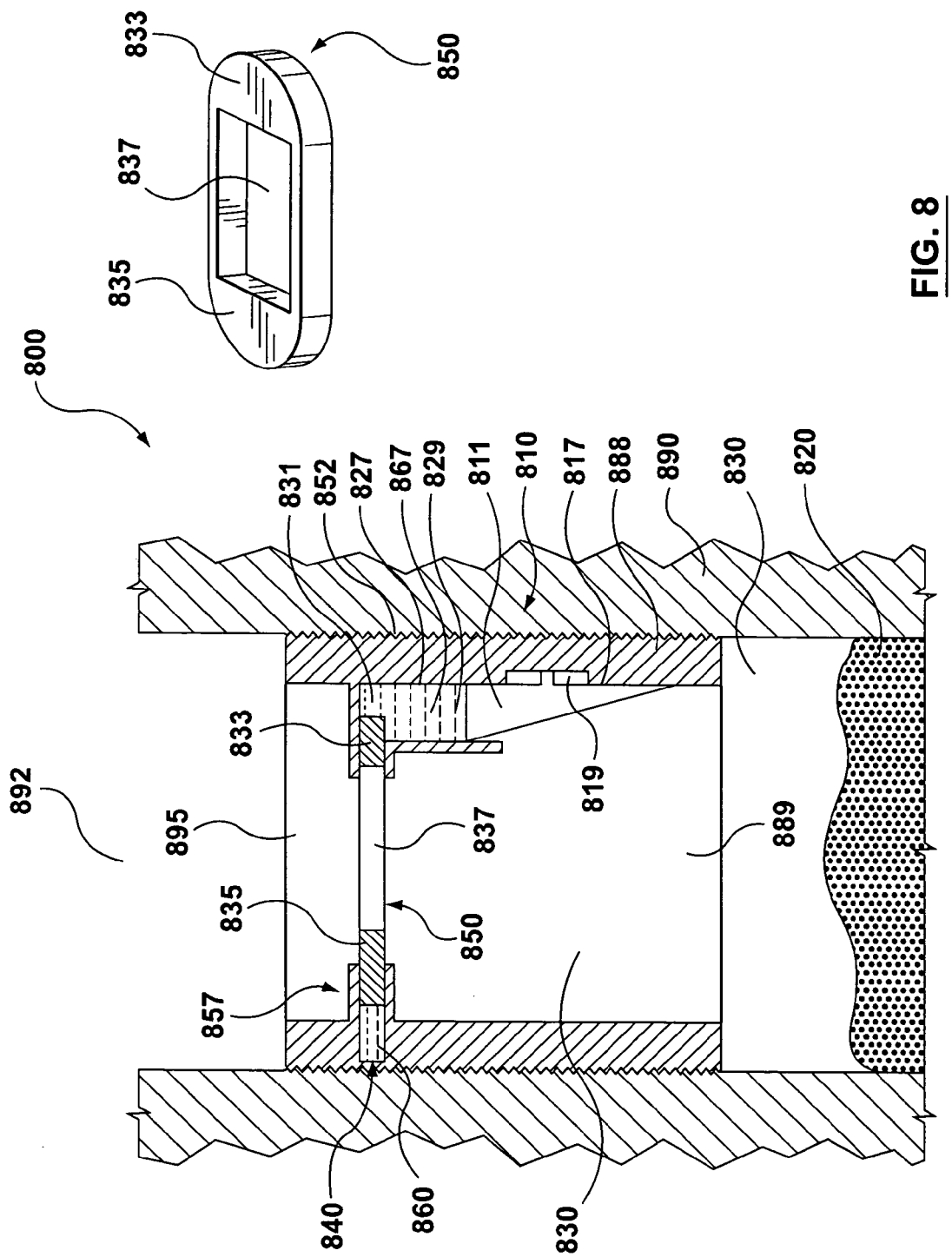
FIG. 8 is a cross sectional view of a molding system according to an eighth exemplary embodiment.

FIG. 8 is a cross sectional view of a molding system 800 (hereafter referred to as the "system 800") according to the eighth exemplary embodiment. To facilitate an understanding of the eighth exemplary embodiment, elements of the eighth exemplary embodiment (that are similar to those of the first exemplary embodiment) are identified by reference numerals that use an eight-hundred designation rather than a one-hundred designation (as used in the first exemplary embodiment). For example, the sensor of the eighth exemplary embodiment is labeled 810 rather than being labeled 110. A viscous-drag sensor 810 (hereafter referred to as the "sensor 810") is interactable with a molding material 820 that is flowable along a melt pathway 830 of the system 800. The sensor 810 is positioned in the melt pathway 830. The melt pathway 830 extends through a manifold 890 and ends at a gate 892 that leads into a mold cavity defined by a mold (not depicted). The location of the sensor 810 in the melt pathway 830 is such that flow characteristics (of the molding material 820) are adjustable or controllable prior to the molding material 820 reaching the gate 892.

Preferably, the sensor 810 includes: (i) a hollow housing 888 (preferably, tubular in shape) that is received into the melt pathway 830 (and is secured to the melt pathway 830), (ii) a blockage pathway 850 having a body 811 that is separate from the blockage pathway 850, and that is slidable in a fluid channel 827 that is defined by the hollow housing 888. The hollow housing 888 (hereafter referred to as the "housing 888") has a cross-sectional shape that is substantially similar to the cross-sectional shape of the melt pathway 830 in order to be sealably received in the melt pathway 830 at a location upstream of the gate 892. The housing 888 has an entrance 889 that allows the molding material 820 to enter and to travel through the housing 888. The housing 888 also has an exit 895 that allows the molding material 820 to exit back into the melt pathway 830 downstream of the entrance 889 on its way to the gate 892. Preferably, a set of threads 852 is located on the outside of the housing 888 in order to threadably tighten the housing 888 to the melt pathway 830. According to a variant, the housing 888 is press fit into the melt pathway 830; according to another variant, the housing 888 is attached to the melt pathway 830. The housing 888 is configured to: (i) allow the molding material 820 to pass therethrough from the entrance 889 to the exit 895 by forming a continuation of the melt pathway 830 and (ii) contain the body 811, the fluid channel 827 and the pathway blockage 850 between the entrance 889 and the exit 895.

The body 811 is configured to be flat and abutable against an inner housing wall 817 of the housing 888. The body 811 is slidably retained along the inner housing wall 817 so that the body 811 may reciprocate along the direction of travel of the molding material 820. A groove 819 is defined in the inner housing wall 817. The groove 819 is used to (i) slidably retain the body 811 and (ii) limit sliding of the body 811 between a high-flow position and a low-flow position. The fluid channel 827 has: (i) a first channel end 829 beginning in the housing 888 at a first location adjacent to the inner housing wall 817 and (ii) a second channel end 831 ending in the housing 888 at a second location. The first location is positioned closer to the entrance 889, while the second location is positioned closer to the exit 895. The two channel ends 829, 831 define the fluid channel 827 therebetween aligned adjacent to the melt pathway 830 inside the housing 888. A portion of the body 811 is configured to retainably slide inside the first channel end 829. The portion of the body 811 not inside the first channel end 829 protrudes out of the fluid channel 827 and extends into the inside of the housing 888, towards the entrance 889, where the body 811 interacts with the molding material 820 entering the entrance 889 and passing therethrough.

The pathway blockage 850 is configured to have a first side 833 and a second side 835. A space between the two sides 833, 835 defines a passage 837 for molding material 820 to travel therethrough. The pathway blockage 850 is positionable inside the housing 888 adjacent to the second channel end 831 of the fluid channel 827. The first side 833 of the pathway blockage 850 is slidably retained by the second channel end 831. The pathway blockage 850 is preferably perpendicular in orientation relative to the housing 888. The second channel end 831 ends at a first housing inner surface, the first inner surface defines a portion of the melt pathway 830 traveling through the housing 888. On the opposite side of the first housing inner surface is a second inner surface defining another portion of the melt pathway 830 traveling through the housing 888. The second surface contains a bore 857 configured to be: (i) preferably extending perpendicularly to the melt pathway 830 (the bore 857 extending into the housing 888) and (ii) in the same vertical position in the melt pathway 830 as the second channel end 831. The bore 857 houses an actuator 840 and the second side 835 of the pathway blockage 850. The actuator 840 is configured to be behind the second side 835 in the bore 857 at a location further inside the housing 888 whereas the second side 835 of the pathway blockage 850 is slidably retained by the bore 857 and is configured to extend into the melt pathway 830. The pathway blockage 850 is slidably retained between walls of the melt pathway by having (i) the first side 833 retained by the second channel end 831 located on the inner surface and (ii) the second side 835 retained by the bore 857 located on the second inner surface. The passage 837 is configured to be substantially parallel with the melt pathway 830; the passage 837 provides a path for molding material 820 to pass therethrough on its way from the entrance 889 of the housing 888 to the exit 895. Since the two sides 833, 835 of the pathway blockage 850 are slidably retained by channels in the housing, the passage 837 is allowed to align or misalign with the melt pathway 830 depending on the position the pathway blockage 850. The passage 837 outline is preferably rectangular shaped and the size of the rectangle is preferably equal to that of the melt pathway 830 in order to allow melt flow therethrough upon perfect alignment with the melt pathway 830. According to a variant, the passage 837 is square shaped; according to another variant the passage 837 is circular shaped.

The fluid channel 827 preferably contains an incompressible fluid 867 (hereafter referred to as the "fluid 867") in order to establish fluid communication between the body 811 and the first side 833 of the pathway blockage 850. According to a variant, the fluid 867 is a compressible fluid. The fluid 867 allows for a force to be transmitted between the body 811 and the pathway blockage 850. The size of the passage 837 increases or decreases as the sensor 810 becomes translated due to the body 811 responding to drag imparted to the body 811 from the molding material 820 so that flow of molding material 820 to the gate 892 may increase or decrease. Translational displacement of the sensor 810 is achieved when the molding material 820 flows over the body 811 and then imparts a viscous drag force to the body 811. The viscous drag force is transmitted from the body, through the incompressible fluid and to the pathway blockage 850, creating translational motion at a distance from the viscous drag sensing point. If the molding material 820 has a high viscosity, a greater drag force is imparted to the sensor 810 and in turn a greater translational displacement of the sensor 810 is achieved so that the passage 837 is widened due to close alignment of the pathway blockage 850 relative to the melt pathway 830. Once the passage 837 is widened, the flow rate of the molding material 820 increases through the pathway blockage 850 allowing additional molding material 820 to reach the gate 892. If the molding material 820 has a low viscosity or is relatively thin, a smaller drag force is imparted to the sensor 810 and in turn a smaller displacement of the sensor 810 is achieved so that the passage 837 is decreased in size due to misalignment of the pathway blockage 850 with the melt pathway 830 (so as to increase blocking of the passage 837). Once the passage 837 is decreased in size, the flow rate of the molding material 820 decreases through the melt pathway 830 allowing less molding material 820 to reach the gate 892.

The actuator 840 is coupled to the second side 835 of pathway blockage 850. The actuator 840 is used to bias translational motion (toward the left side of FIG. 8, for example) of the pathway blockage 850 and the body 811 in order to control alignment of the pathway blockage 850 relative to the melt pathway 830. The alignment of the pathway blockage 850 relative to the melt pathway 830 defines or controls the size of the passage 837. The actuator 840 is mounted in the bore 857 of the housing 888. The actuator 840 is preferably a compressible gas 860 (hereafter referred to as the "gas 860").

The gas 860 is used to bias translational movement of the pathway blockage 850 and body 811. The gas 860 biases the passage 837 of the pathway blockage 850 to misalign with the melt pathway 830. The gas 860 biasing direction is in the opposite direction of translational displacement Induced on the pathway blockage 850 and body 811 by the viscous drag force. As the molding material 820 flows past the body 811, the molding material 820 imparts a viscous drag force to the body 811. The viscous drag force slidably translates the body 811 further into the fluid channel 827 producing a force on the incompressible fluid. This force is further translated from the first channel end 829, down the fluid 867 and to the second channel end 831 where it transmits a hydraulic force on the pathway blockage 850, thus creating closer alignment of the pathway blockage 850 with the melt pathway 830 and thus creating a larger size of the passage 837. Responsive to the pathway blockage 850 translating due to the viscous drag force imparted to the pathway blockage 850 by the molding material 820, the gas 860 stores potential energy and creates a biasing force in the opposite direction of translation in order to reduce the translational displacement (misalignment) created by the viscous drag force and to control the size of passage 837. The gas 860 creates different translational forces so as to vary the alignment of the pathway blockage 850 and in turn vary the size of the passage 837 with different drag conditions. If a high-viscosity molding material 820 flows past the body 811, (i) a high viscous drag force will be imparted to the body 811 and (ii) the gas 860 will store more potential energy, and the gas 860 biases the translational displacement (misalignment) of the pathway blockage 850 by a smaller amount which results in a larger size of the passage 837 and a higher flow rate of molding material 820 past the pathway blockage 850. If a low-viscosity molding material 820 flows past the body 811, (i) a low viscous drag force will be imparted on the body 811 and (ii) the gas 860 will store less potential energy, and the gas 860 biases the translational displacement (misalignment) of the pathway blockage 850 by a larger amount which results in a smaller size of the passage 837 and a lower flow rate of molding material 820 past the pathway blockage 850. Responsive to the sensor 810 sensing viscous-drag force, the gas 860 actuatably translates the pathway blockage 850 to amend (that is, increase or decrease) the alignment of the pathway blockage 850 with the melt pathway 830 so that flow of the molding material 820 through the passage 837 and melt pathway 830 varies.

Figure 9:
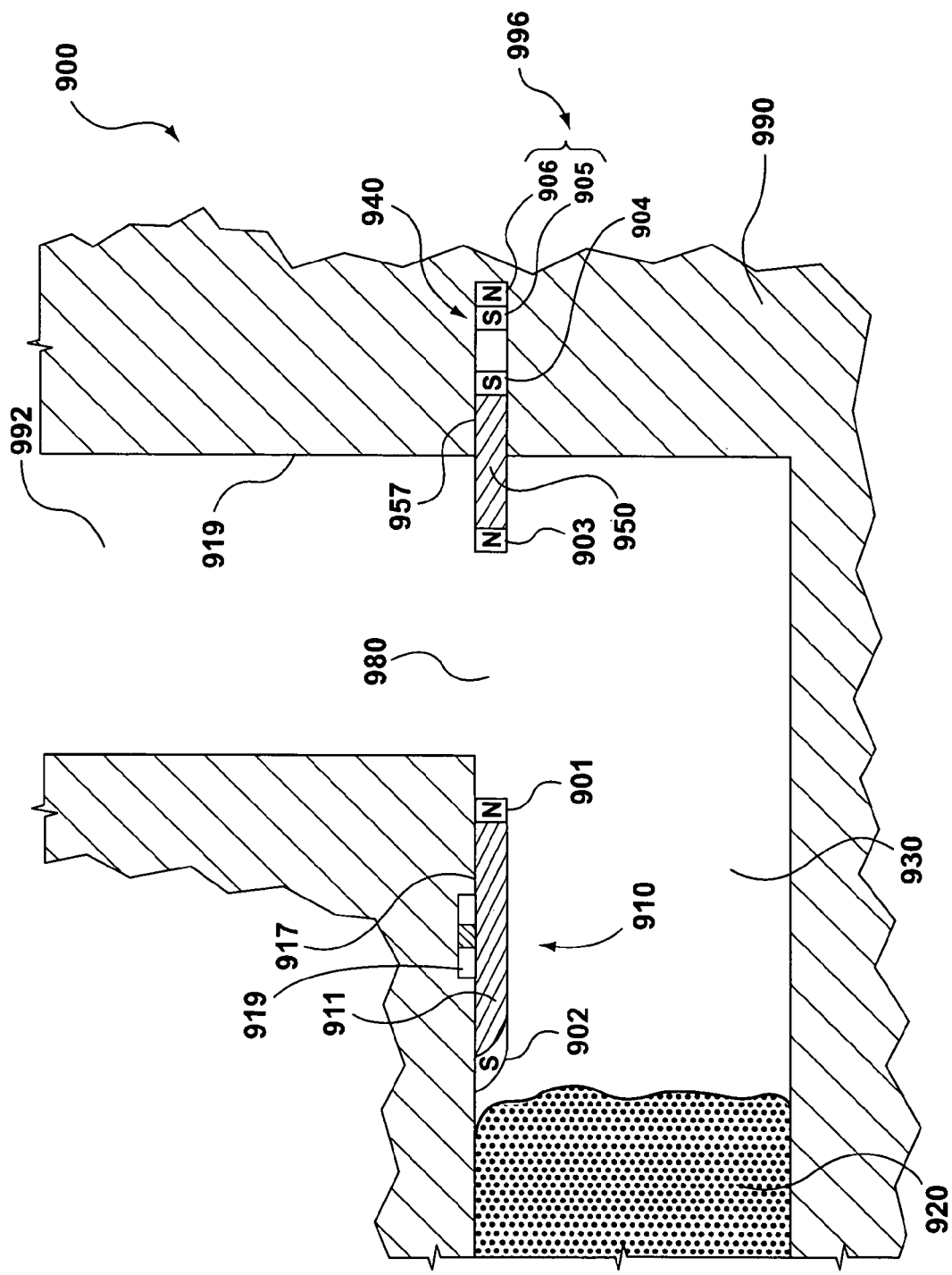
FIG. 9 is a cross sectional view of a molding system according to a ninth exemplary embodiment.

FIG. 9 is a cross sectional view of a molding system 900 (hereafter referred to as the "system 900") according to the ninth exemplary embodiment. To facilitate an understanding of the ninth exemplary embodiment, elements of the ninth exemplary embodiment (that are similar to those of the first exemplary embodiment) are identified by reference numerals that use a nine-hundred designation rather than a one-hundred designation (as used in the first exemplary embodiment). For example, the sensor of the ninth exemplary embodiment is labeled 910 rather than being labeled 110.

A viscous-drag sensor 910 (hereafter referred to as the "sensor 910") is interactable with a molding material 920 that is flowable along a melt pathway 930 of the system 900. The sensor 910 is positioned in the melt pathway 930. The melt pathway 930 extends through a manifold 990 and ends at a gate 992 that leads into a mold cavity defined by a mold (not depicted). The location of the sensor 910 in the melt pathway 930 is such that flow characteristics (of the molding material 920) are adjustable or controllable prior to the molding material 920 reaching the gate 992.

Preferably, the sensor 910 includes a pathway blockage 950 having a magnetic body 911 (hereafter referred to as the "body 911") that is separate from the pathway blockage 950. The body 911 is configured to be flat and abutable against a first manifold wall 917 in the melt pathway 930. The body 911 is slidably retained along the first manifold wall 917 so that the body 911 may reciprocate. A groove 919 is defined in the first manifold wall 917 and the groove 919 is used to limit sliding of the body 911 between a high-flow position and a low-flow position. The body 911 is preferably made of a magnetic material having two magnetic poles (a body first pole 901 and a body second pole 902). The body first pole 901 and the body second pole 902 are: (i) opposite polarities such as north and south and (ii) spaced apart and located on opposite ends of the body 911. According to a variant, the body 911 is an electromagnet having two electrically-induced magnetic poles. The body first pole 901 is located downstream of the body second pole 902. A bore 957, located on a second manifold wall 919, is configured to slidably retain a pathway blockage 950 as well as an actuator 940. The bore 957 is preferably perpendicular in orientation relative to the melt pathway 930. The second manifold wall 919 is located opposite of the first manifold wall 917 and forms the second side of a melt pathway 930. Together, the first and second manifold walls 917, 919 form a portion of the melt pathway 930 for the molding material 920 to travel through on its way to the gate 992. The bore 957 is located on a level identical to that of the body 911. The longitudinal axis of the body 911 is aligned with the longitudinal axis of the bore 957. The actuator 940 is located behind the pathway blockage 950 inside the bore 957 at a location further inside the manifold 990. The pathway blockage 950 is slidably retained by the bore 957 and is configured to partially extend into the melt pathway 930.

The pathway blockage 950 is a magnet having a body first pole 903 and a body second pole 904. The body first pole 903 extends into the melt pathway 930 in order to provide a restriction for flowing molding material 920; the size of the restriction depends on the viscosity of the molding material 920. The body second pole 904 is on the pathway blockage side located inside the bore 957 while the body second pole 904 is configured to magnetically interact with the actuator 940. Because the body 911 and the pathway blockage 950 are both magnets, they magnetically interact with each other. Movement of the body 911 due to the viscous drag force imparted on it causes flow of the molding material 920 to vary in the following manner: (i) if the molding material 920 has a low viscosity, the sensor 910 reacts to reduce the rate of flow of the molding material 920, and/or (ii) if the molding material 920 has a high viscosity, the sensor 910 reacts to increase the rate of flow of the molding material 920. In this manner, the molding material 920 is made to flow and interact with the sensor 910 and does not (preferably) substantially bypass the sensor 910. A gap 980 is defined between the body 911 and the pathway blockage 950. The gap 980 is configured to provide a path for molding material 920 to pass therethrough on the way to the gate 992. The size of the gap 980 increases or decreases as the sensor 910 becomes translated due to the body 911 responding to drag imparted to the body 911 from the molding material 920 so that flow of molding material 920 to the gate 992 may increase or decrease. Translational displacement of the sensor 910 is achieved when the molding material 920 flows over the body 911 and then imparts a viscous drag force to the body 911. If the molding material 920 has a high viscosity, a greater drag force is imparted to the body 911 and in turn a greater translational displacement of the body 911 achieved. This greater translational displacement causes the body 911 to get closer to the pathway blockage 950. Since both the pathway blockage 950 and body 911 are magnets having opposite polarities facing each other, then the gap 980 is widened due to the force induced on the pathway blockage, causing it to slide into the bore 957 and decrease the restriction of molding material flow. Once the gap 980 is widened, the flow rate of the molding material 920 increases through the gap 980 allowing additional molding material 920 to reach the gate 992. If the molding material 920 has a low viscosity or is relatively thin, a smaller drag force is imparted to the sensor 910 and in turn a smaller displacement of the sensor 910 is achieved. This smaller translational displacement induces a smaller force on the pathway blockage 950, failing to move it any further into the bore 957. The pathway blockage 950 remains protruding from the bore 957 creating (i) restriction of molding material 920 flow and (ii) a reduction in gap 980 size. Once the gap 980 is decreased in size, the flow rate of the molding material 920 decreases through the melt pathway 930 allowing less molding material 920 to reach the gate 921.

The actuator 940 is placed adjacent to the body second pole 904. The actuator 940 is used to bias translational motion (toward the left side of FIG. 9, for example) of the pathway blockage 950 in order to control the size of the gap 980. The actuator 940 is mounted in the bore 957 of the second manifold wall 919. The actuator 940 is preferably a magnet 996 (hereafter referred to as the "actuator magnet 996") having an actuator first pole 905 and an actuator second pole 906. The actuator magnet 996 is used to bias translational movement of the pathway blockage 950. According to a variant, a spring is used in place of the body second pole 904, the actuator first pole 905, and the actuator second pole 906. The actuator magnet 996 biasing direction is in the opposite direction of translational displacement induced on the pathway blockage 950 and body 911 by the viscous drag force. As the molding material 920 flows past the body 911, the molding material 920 imparts a viscous drag force to the body 911. The viscous drag force slidably translates the body 911 further downstream in the melt pathway 930 producing a magnetic force on the pathway blockage 950. This magnetic force creates translational motion of the pathway blockage 950 further into the bore 957 and increases the size of the gap 980. Responsive to the pathway blockage 950 translating due to the viscous drag force imparted to the pathway blockage 950 by the molding material 920, the magnet 996 stores potential energy and creates a biasing force in the opposite direction of translation in order to reduce the translational displacement created by the viscous drag force. The actuator magnet 996 in bore 957 has an magnetic orientation opposite of the pathway blockage 950, meaning the actuator first pole 905 (the pole on the side of the actuator magnet 996 closer to the pathway blockage 950) has the same polarity as the body second pole 904. Therefore, as the pathway blockage 950 translates inward into the bore 957, the body second pole 904 gets closer to the actuator first pole 905, creating potential energy and repulsion due to opposite magnetic polarity. The actuator magnet 996 creates different magnetic biasing forces so as to vary the protrusion of the pathway blockage 950 into the melt pathway 930 and in turn vary the size of the gap 980 with different drag conditions. If a high-viscosity molding material 920 flows past the body 911, (i) a high viscous drag force will be imparted to the body 911 and (ii) the actuator magnet 996 will store more potential enemy, and the actuator magnet 996 biases the translational displacement (protrusion) of the pathway blockage 950 by a smaller amount which results in a larger size of the gap 980 and a higher flow rate of molding material 920 past the pathway blockage 950. It a low-viscosity molding material 920 flows past the body 911, (i) a low viscous drag force will be imparted on the body 911 and (ii) the actuator magnet 996 will store less potential energy, and the actuator magnet 996 biases the translational displacement (protrusion) of the pathway blockage 950 by a larger amount which results in a larger size of the gap 980 and a lower flow rate of molding material 920 past the pathway blockage 950. Responsive to the sensor 910 sensing viscous-drag force, the actuator magnet 996 actuatably translates the pathway blockage 950 to amend (that is, increase or decrease) the protrusion of the pathway blockage 950 into the melt pathway 930 so that flow of the molding material 920 through the gap 980 and melt pathway 930 varies.

Figure 10:
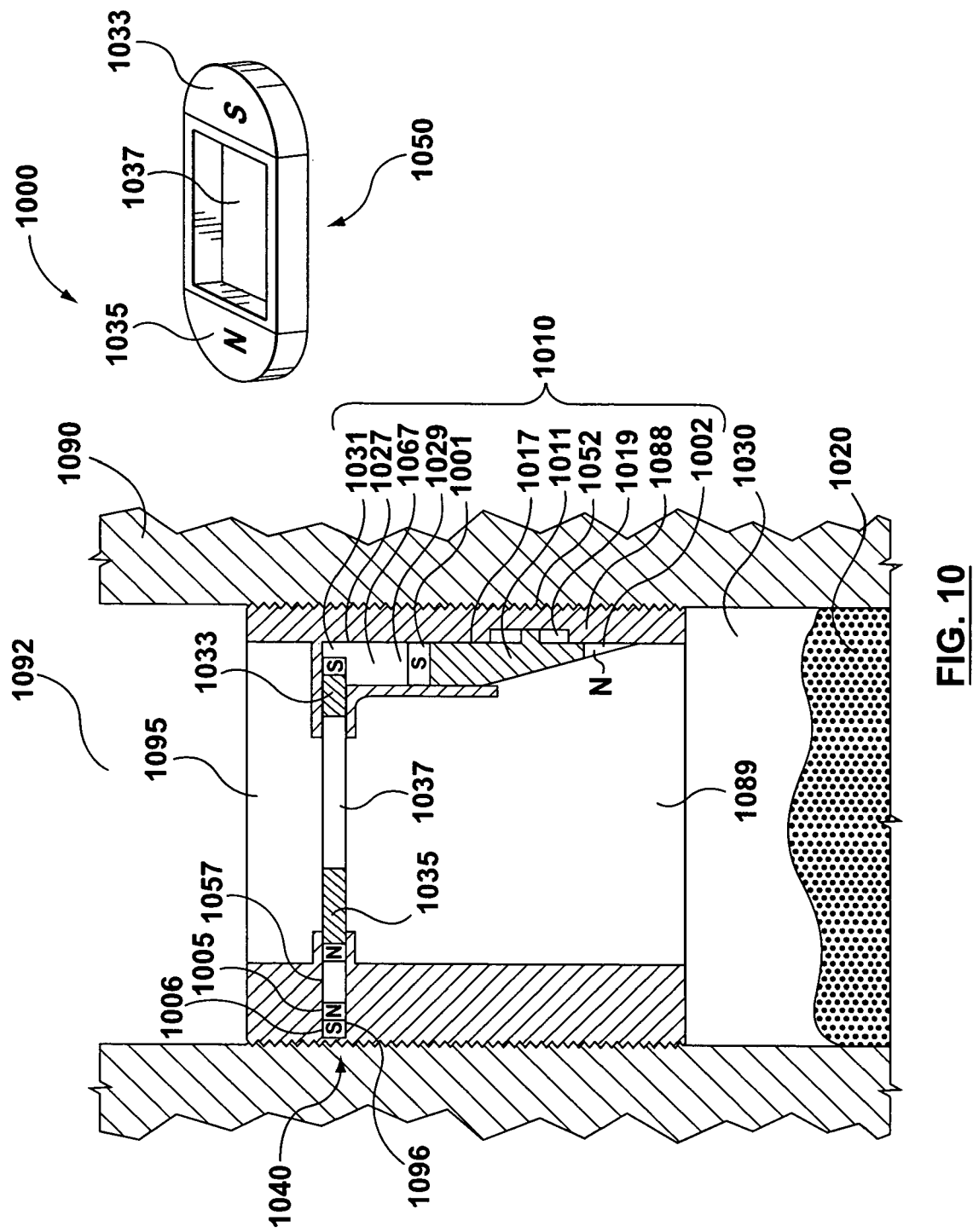
FIG. 10 is a cross sectional view of a molding system according to a tenth exemplary embodiment.

FIG. 10 is a cross sectional view of a molding system 1000 (hereafter referred to as the "system 1000") according to the tenth exemplary embodiment. To facilitate an understanding of the tenth exemplary embodiment, elements of the tenth exemplary embodiment (that are similar to those of the first exemplary embodiment) are identified by reference numerals that use a one-thousand designation rather than a one-hundred designation (as used in the first exemplary embodiment). For example, the sensor of the tenth exemplary embodiment is labeled 1010 rather than being labeled 110. A viscous-drag sensor 1010 (hereafter referred to as the "sensor 1010") is interactable with a molding material 1020 that is flowable along a melt pathway 1030 of the system 1000. The sensor 1010 is positioned in the melt pathway 1030. The melt pathway 1030 extends through a manifold 1090 and ends at a gate 1092 that leads into a mold cavity defined by a mold (not depicted). The location of the sensor 1010 in the melt pathway 1030 is such that flow characteristics (of the molding material 1020) are adjustable or controllable prior to the molding material 1020 reaching the gate 1092.

Preferably, the sensor 1010 includes: (i) a hollow housing 1088 (preferably, tubular in shape) that is received into the melt pathway 1030 (and is secured to the melt pathway 1030), and (ii) a pathway blockage 1050 having a body 1011 that is separate from the pathway blockage 1050 slidable in a channel 1027 that is defined by the hollow housing 1088, and the pathway blockage 1050 is slidably mounted to the hollow housing 1088. The hollow housing 1088 (hereafter referred to as the "housing 1088") has a cross-sectional shape that is substantially similar to the cross-sectional shape of the melt pathway 1030 in order to be sealably received in the melt pathway 1030 at a location upstream of the gate 1092. The housing 1088 has an entrance 1089 that allows the molding material 1020 to enter and to travel through the housing 1088. The housing 1088 also has an exit 1095 that allows the molding material 1020 to exit back into the melt pathway 1030 downstream of the entrance 1089 on its way to the gate 1092. A set of threads 1052 is located on the outside of the housing 1088 in order to threadably tighten or engage the housing 1088 to the melt pathway 1030. According to a variant, the housing 1088 is press fit into the melt pathway 1030; according to another variant, the housing 1088 is securely or fixedly attached to the melt pathway 1030. The housing 1088 is configured to: (i) allow the molding material 1020 to pass therethrough from the entrance 1089 to the exit 1095 by forming a continuation of the melt pathway 1030 and (ii) structurally position the body 1011, the channel 1027 and the pathway blockage 1050 between the entrance 1089 and the exit 1095.

The body 1011 is configured to be flat and abutable against an inner housing wall 1017 of the housing 1088. The body 1011 is slidably retained along the inner housing wall 1017 so that the body 1011 may reciprocate along the direction of travel of the molding material 1020. A groove 1019 is defined in the inner housing wall 1017. The groove 1019 is used to (i) slidably retain the body 1011 and (ii) limit sliding of the body 1011 between a high-flow position and a low-flow position.

The body 1011 is preferably made of a magnetic material having two magnetic poles (a body first pole 1001 and a body second pole 1002). The body first pole 1001 and body second pole 1002 are: (i) opposite polarities such as north and south and (ii) spaced apart and located on opposite ends of the body 1011. According to a variant, the body 1011 is an electromagnet having two electrically-induced magnetic poles. The body first pole 1001 is located downstream of the body second pole 1002. The channel 1027 has: (i) a first channel end 1029 beginning in the housing 1088 at a first location adjacent to the inner housing wall 1017 and (ii) a second channel end 1031 ending in the housing 1088 at a second location. The first location is positioned closer to the entrance 1089, while the second location is positioned closer to the exit 1095. The two channel ends 1029, 1031 define the channel 1027 therebetween aligned adjacent to the melt pathway 1030 inside the housing 1088. A portion of the body 1011 is configured to retainably slide inside the first channel end 1029. The portion of the body 1011 not inside the first channel end 1029 protrudes out of the mild-channel 1027 and extends into the inside of the housing 1088, towards the entrance 1089, where the body 1011 interacts with the molding material 1020 entering the entrance 1089 and passing therethrough.

Preferably, the pathway blockage 1050 includes a magnet (or magnetic material), the pathway blockage 1050 having a first block pole 1033 and a second block pole 1035. A space between the first block pole 1033 and the second block pole 1035 define a passage 1037 for molding material 1020 to travel therethrough. The pathway blockage 1050 is positioned inside the housing 1088 adjacent to the second channel end 1031 of the channel 1027. The first block pole 1033 of the pathway blockage 1050 is slidably retained in the second channel end 1031. The pathway blockage 1050 is preferably perpendicular in orientation relative to the housing 1088. The second channel end 1031 ends at a first housing inner surface, the first inner surface defines a portion of the melt pathway 1030 traveling through the housing 1088. On the opposite side of the first housing inner surface is a second inner surface defining another portion of the melt pathway 1030 traveling through the housing 1088. The second surface contains a bore 1057 that preferably extends (i) perpendicularly to the melt pathway 1030 (the bore 1057 extending into the housing 1088) and (ii) in the same vertical position in the melt pathway 1030 as the second channel end 1031. The bore 1057 houses an actuator 1040 and the second block pole 1035 of the pathway blockage 1050. The actuator 1040 is positioned behind the second block pole 1035 in the bore 1057 at a location further inside the housing 1088, whereas the second block pole 1035 of the pathway blockage 1050 is (i) slidably retained by the bore 1057 and (i) extends into the melt pathway 1030. The pathway blockage 1050 is slidably retained between walls of the melt pathway by having (i) the first block pole 1033 retained by the second channel end 1031 located on the inner surface and (ii) the second block pole 1035 retained by the bore 1057 located on the second Inner surface. The passage 1037 is substantially parallel with the melt pathway 1030; the passage 1037 provides a path for molding material 1020 to pass therethrough on its way from the entrance 1089 of the housing 1088 to the exit 1095. Since the first block pole 1003 and the second block pole 1035 of the pathway blockage 1050 are slidably retained by channels in the housing, the passage 1037 is allowed to align or misalign with the melt pathway 1030 depending on the position the pathway blockage 1050. The passage 1037 outline is preferably rectangular shaped and the size of the rectangle is preferably equal to that of the melt pathway 1030 in order to allow melt flow therethrough upon perfect alignment with the melt pathway 1030.

According to a variant, the passage 1037 is square shaped; according to another variant the passage 1037 is circular shaped.

The channel 1027 preferably contains an empty space (or channel) 1067 (hereafter referred to as the "space 1067") that is defined by a tube. The tube and the space 1067 allow the body 1011 to be retainably, slidably movable along the inner housing wall 1017 so that the body first pole 1001, and the first block pole 1033 may be brought movably interactable relative to each other. The size of the passage 1037 increases or decreases as the body 1011 of the sensor 1010 becomes translated due to the body 1011 receiving (responding to) drag imparted by the molding material 1020, so that flow of molding material 1020 to the gate 1092 may be increased or decreased. Translational displacement of the sensor 1010 is achieved when the molding material 1020 flows over the body 1011 and then imparts a viscous drag force to the body 1011 causing the body 1011 to slide upwardly into the first channel end 1029 and closer to the second channel end 1031 (which contains the pathway blockage 1050). Because the body 1011 and the pathway blockage 1050 include magnets, they are magnetically interactable with each other. Since the body first pole 1001 and the first block pole 1033 are preferably similar (that is, they have the same magnetic polarity), then movement of the body 1011 towards the pathway blockage 1050 will create a magnetic repulsion force that travels through the space 1067. Once the body 1011 is translated further into channel 1027 due to the viscous drag force imparted to the body 1011 by the molding material 1020, the pathway blockage 1050: (i) feels or senses a magnetic force on the first block pole and (ii) adjusts its position by translating in the housing 1088 and creating alignment or misalignment of the passage 1037 with the melt pathway 1030. Movement of the body 1011 due to the viscous drag force imparted on it causes flow of the molding material 1020 to vary in the following manner: (i) if the molding material 1020 has a low viscosity, the sensor 1010 reacts to reduce the rate of flow of the molding material 1020, and/or (ii) if the molding material 1020 has a high viscosity, the sensor 1010 reacts to increase the rate of flow of the molding material 1020. In this manner, the molding material 1020 is made to flow and interact with the sensor 1010 and does not (preferably) substantially bypass the sensor 1010. If the molding material 1020 has a high viscosity, a greater drag force is imparted to the sensor 1010 and in turn a greater translational displacement of the sensor 1010 is achieved so that the passage 1037 is widened due to close alignment of the pathway blockage 1050 relative to the melt pathway 1030. Once the passage 1037 is widened, the flow rate of the molding material 1020 increases through the pathway blockage 1050 allowing more molding material 1020 to reach the gate 1092. If the molding material 1020 has a low viscosity or is relatively thin, a smaller drag force Is imparted to the sensor 1010 and in turn a smaller displacement of the sensor 1010 is achieved so that the passage 1037 is decreased in size due to misalignment of the pathway blockage 1050 with the melt pathway 1030 (so as to increase blocking of the passage 1037). Once the passage 1037 is decreased In size, the flow rate of the molding material 1020 decreases through the melt pathway 1030 allowing less molding material 1020 to reach the gate 1092.

The actuator 1040 is coupled to the second block pole 1035 of pathway blockage 1050. The actuator 1040 is used to bias translational motion (toward the right side of FIG. 10, for example) of the pathway blockage 1050 and the body 1011 in order to control alignment of the pathway blockage 1050 relative to the melt pathway 1030. The alignment of the pathway blockage 1050 relative to the melt pathway 1030 defines the size of the passage 1037. The actuator 1040 is mounted in the bore 1057 of the housing 1088. The actuator 1040 includes a magnet 1096 (hereafter referred to as the "actuator magnet 1096") having an actuator first pole 1005 and an actuator second pole 1006. According to a variant (not depicted), a spring is used in place of the actuator first pole 1005, the actuator second pole 1006, and the magnet mounted in the pathway blockage 1050. The actuator first pole 1005 is configured to lay closer to the second block pole 1035 of the pathway blockage 1050. The actuator magnet 1096 is used to bias translational movement of the pathway blockage 1050 and body 1011. The actuator magnet 1096 biases the passage 1037 of the pathway blockage 1050 to misalign with the melt pathway 1030. The actuator magnet 1096 biasing direction is in the opposite direction of translational displacement induced on the pathway blockage 1050 and body 1011 by the viscous drag force. As the molding material 1020 flows past the body 1011, the molding material 1020 imparts a viscous drag force to the body 1011. The viscous drag force slidably translates the body 1011 further into the channel 1027 producing a magnetic force on the pathway blockage 1050. This magnetic force is translated from the first channel end 1029, down the space 1067 and to the second channel end 1031 where it transmits the magnetic force on the pathway blockage 1050, thus creating closer alignment of the pathway blockage 1050 with the melt pathway 1030 and thus creating a larger size of the passage 1037. Responsive to the pathway blockage 1050 translating due to the viscous drag force imparted to the pathway blockage 1050 by the molding material 1020, the actuator magnet 1096 stores potential energy (in the form of two interactive magnets having opposite polarities) and creates a magnetic biasing force in the opposite direction of translation in order to reduce the translational displacement (alignment) created by the viscous drag force and to control the size of passage 1037. The actuator magnet 1098 creates the magnetic biasing force by having its actuator first pole 1005 interact with the second block pole 1035 of the pathway blockage 1050. Since both the actuator first pole 1005 and the second block pole have the same magnetic polarity, they repel each other, allowing the actuator magnet 1096 to bias the pathway blockage 1050. The actuator magnet 1096 creates different magnetic forces so as to vary the alignment of the pathway blockage 1050 and in turn vary the size of the passage 1037 with different drag conditions. If a high-viscosity molding material 1020 flows past the body 1011, (i) a high viscous drag force will be imparted to the body 1011 and (ii) the actuator magnet 1096 will store more potential energy, and the actuator magnet 1096 biases the translational displacement (misalignment) of the pathway blockage 1050 by a smaller amount which results in a larger size of the passage 1037 and a higher flow rate of molding material 1020 past the pathway blockage 1050. If a low-viscosity molding material 1020 flows past the body 1011, (i) a low viscous drag force will be imparted on the body 1011 and (ii) the actuator magnet 1096 will store less potential energy, and the actuator magnet 1096 biases the translational displacement (misalignment) of the pathway blockage 1050 by a larger amount which results in a smaller size of the passage 1037 and a lower flow rate of molding material 1020 past the pathway blockage 1050. Responsive to the sensor 1010 sensing viscous-drag force, the actuator magnet 1096 actuatably translates the pathway blockage 1050 to amend (that is, increase or decrease) the alignment of the pathway blockage 1050 with the melt pathway 1030 so that flow of the molding material 1020 through the passage 1037 and melt pathway 1030 varies.

The description of the exemplary embodiments provides examples of the present invention, and these examples do not limit the scope of the present invention. It is understood that the scope of the present invention is limited by the claims. The concepts described above may be adapted for specific conditions and/or functions, and may be further extended to a variety of other applications that are within the scope of the present invention. Having thus described the exemplary embodiments, it will be apparent that modifications and enhancements are possible without departing from the concepts as described. Therefore, what is to be protected by way of letters patent are limited only by the scope of the following claims:

The invention claimed is:

1. A molding system, comprising:
   a melt pathway being configured to convey a molding material; and
   a viscous-drag sensor being configured to move along the melt pathway, the viscous-drag sensor including:
      a pathway blockage being movable along the melt pathway, the pathway blockage being movable along a first direction to further open the melt pathway, and the pathway blockage being movable along a second direction to further close the melt pathway; and
      an actuator being coupled with the pathway blockage, the actuator biasing the pathway blockage to vary the melt pathway while the molding material drags along and moves the pathway blockage, and responsive to the pathway blockage sensing a viscous-drag force, the pathway blockage acts to: (i) further open the melt pathway if a viscosity of the molding material is high, and (ii) further close the melt pathway if the viscosity of the molding material is low.

2. The molding system of claim 1, wherein:
   responsive to the pathway blockage sensing the viscous-drag force, the actuator moves the pathway blockage responsive to the pathway blockage sensing drag from the molding material, and a flow of the molding material through the melt pathway varies as the pathway blockage moves relative to the melt pathway.

3. A molding system, comprising:
   a melt pathway being configured to convey a molding material; and
   a viscous-drag sensor being configured to move along the melt pathway, the viscous-drag sensor including:
      a pathway blockage being movable along the melt pathway, the pathway blockage being movable along a first direction to further open the melt pathway, and the pathway blockage being movable along a second direction to further close the melt pathway, and
      an actuator being coupled with the pathway blockage, the actuator biasing the pathway blockage to vary the melt pathway while the molding material drags along and moves the pathway blockage, and responsive to the pathway blockage sensing a viscous-drag force, the pathway blockage acts to: (i) further open the melt pathway if a viscosity of the molding material is high, and (ii) further close the melt pathway if the viscosity of the molding material is low,
   wherein movement of the pathway blockage causes flow of the molding material:
      (i) to reduce a rate of flow of the molding material if the molding material has a low viscosity, and
      (ii) to increase the rate of flow of the molding material if the molding material has a high viscosity.

4. A molding system, comprising:
a melt pathway being configured to convey a molding material; and
a viscous-drag sensor being configured to move along the melt pathway, the viscous-drag sensor including:
   a pathway blockage being movable along the melt pathway, the pathway blockage being movable along a first direction to further open the melt pathway, and the pathway blockage being movable along a second direction to further close the melt pathway; and
   an actuator being coupled with the pathway blockage, the actuator biasing the pathway blockage to vary the melt pathway while the molding material drags along and moves the pathway blockage, and responsive to the pathway blockage sensing a viscous-drag force, the pathway blockage acts to: (i) further open the melt pathway if a viscosity of the molding material is high, and (ii) further close the melt pathway if the viscosity of the molding material is low,
wherein an amount of drag sensed by the viscous-drag sensor is a function of intrinsic properties of the viscosity of the molding material.

5. A molding system, comprising:
a melt pathway being configured to convey a molding material; and
a viscous-drag sensor being configured to move along the melt pathway, the viscous-drag sensor including:
   a pathway blockage being movable along the melt pathway, the pathway blockage being movable along a first direction to further open the melt pathway, and the pathway blockage being movable along a second direction to further close the melt pathway; and
   an actuator being coupled with the pathway blockage, the actuator biasing the pathway blockage to vary the melt pathway while the molding material drags along and moves the pathway blockage, and responsive to the pathway blockage sensing a viscous-drag force, the pathway blockage acts to: (i) further open the melt pathway if a viscosity of the molding material is high, and (ii) further close the melt pathway if the viscosity of the molding material is low,
wherein an amount of drag sensed by the viscous-drag sensor is a function of:
   intrinsic properties of the viscosity of the molding material,
   a type of material that the viscous-drag sensor is made from, and
   a type of surface finish of the viscous-drag sensor that comes into contact with the molding material.

6. A molding system, comprising:
a melt pathway being configured to convey a molding material; and
a viscous-drag sensor being configured to move along the melt pathway, the viscous-drag sensor including:
   a pathway blockage being movable along the melt pathway, the pathway blockage being movable along a first direction to further open the melt pathway, and the pathway blockage being movable along a second direction to further close the melt pathway; and
   an actuator being coupled with the pathway blockage, the actuator biasing the pathway blockage to vary the melt pathway while the molding material drags along and moves the pathway blockage, and responsive to the pathway blockage sensing a viscous-drag force, the pathway blockage acts to: (i) further open the melt pathway if a viscosity of the molding material is high, and (ii) further close the melt pathway if the viscosity of the molding material is low,
wherein responsive to the viscous-drag sensor sensing the viscous-drag force, the actuator moves the viscous-drag sensor responsive to the viscous-drag sensor sensing drag from the molding material, and a flow of the molding material through the melt pathway varies as the viscous-drag sensor moves relative to the melt pathway.

7. A molding system, comprising:
a melt pathway being configured to convey a molding material; and
a viscous-drag sensor being configured to move along the melt pathway, the viscous-drag sensor including:
   a pathway blockage being movable along the melt pathway, the pathway blockage being movable along a first direction to further open the melt pathway, and the pathway blockage being movable along a second direction to further close the melt pathway; and
   an actuator being coupled with the pathway blockage, the actuator biasing the pathway blockage to vary the melt pathway while the molding material drags along and moves the pathway blockage, and responsive to the pathway blockage sensing a viscous-drag force, the pathway blockage acts to: (i) further open the melt pathway if a viscosity the molding material is high, and (ii) further close the melt pathway if the viscosity of the molding material is low,
wherein the actuator is configured to bias the viscous-drag sensor in one direction while the viscous-drag force moves the viscous-drag sensor in an opposite direction.

8. A molding system, comprising:
a melt pathway being configured to convey a molding material; and
a viscous-drag sensor being configured to move along the melt pathway, the viscous-drag sensor including:
   a pathway blockage being movable along the melt pathway, the pathway blockage being movable along a first direction to further open the melt pathway, and the pathway blockage being movable along a second direction to further dose the melt pathway; and
   an actuator being coupled with the pathway blockage, the actuator biasing the pathway blockage to vary the melt pathway while the molding material drags along and moves the pathway blockage, and responsive to the pathway blockage sensing a viscous-drag force, the pathway blockage acts to: (i) further open the melt pathway if a viscosity of the molding material is high, and (ii) further close the melt pathway if the viscosity of the molding material is low,
wherein a net movement of the actuator is configured to control flow of the molding material.

9. The molding system of claim 1, wherein:
the actuator includes:
   a spring being coupled to the pathway blockage.

10. The molding system of claim 1, wherein:
the actuator includes:
   a spring being coupled to the pathway blockage, the spring being configured to bias the pathway blockage in one direction to close the melt pathway while the molding material moves the pathway blockage in an opposite direction to open the melt pathway.

11. The molding system of claim 1, wherein:
the actuator includes a linear force spring.

12. The molding system of claim 1, wherein:
the actuator includes:
   a leaf spring.

13. The molding system of claim 1, wherein:
the actuator includes:
a torsional spring.

14. The molding system of claim 1, wherein:
the actuator includes:
an electric motor.

15. The molding system of claim 1, wherein:
the actuator includes:
a compressible fluid.

16. The molding system of claim 1, wherein:
the actuator includes:
a magnet.

17. The molding system of claim 1, wherein:
the viscous-drag sensor further includes:
a hollow tube being configured to receive the pathway blockage, the hollow tube defining a portal that is closable and openable by the pathway blockage, the actuator coupling the pathway blockage to a manifold of the molding system, and the actuator biasing the pathway blockage to constrict the melt pathway.

18. The molding system of claim 1, wherein:
the actuator includes:
a spring being coupled to the pathway blockage, the spring being configured to bias the pathway blockage in one direction to close the melt pathway while the molding material moves the pathway blockage in an opposite direction to open the melt pathway, and the pathway blockage defining a portal being closable and being openable relative to the melt pathway.

19. The molding system of claim 1, wherein:
the actuator includes:
a leaf spring being coupled to the pathway blockage.

20. The molding system of claim 1, wherein:
the actuator includes:
a leaf spring being coupled to the pathway blockage, the leaf spring being configured to bias the pathway blockage in one direction while the molding material moves the pathway blockage in an opposite direction.

21. The molding system of claim 1, wherein:
the actuator includes:
a leaf spring being coupled to the pathway blockage, the leaf spring being configured to bias the pathway blockage in one direction to close the melt pathway while the molding material moves the pathway blockage in an opposite direction to open the melt pathway.

22. The molding system of claim 1, wherein:
the viscous-drag sensor further includes:
an arm, the arm being configured to define a portal being closable and openable relative to the melt pathway, and the actuator includes:
a torsional spring, the torsional spring being configured to couple an end of the pathway blockage to an end of the arm.

23. The molding system of claim 1, wherein:
the viscous-drag sensor further includes:
an arm, the arm being configured to define a portal that is crosable and openable relative to the melt pathway, and the actuator includes:
a torsional spring, the torsional spring being configured to couple an end of the pathway blockage to an end of the arm, so that the molding material may slide the pathway blockage in one direction while the torsional spring biases the pathway blockage in an opposite direction.

24. The molding system of claim 1, wherein:
the viscous-drag sensor further includes:
an arm, the arm being configured to define a portal being closable and openable relative to the melt pathway, and the actuator includes:
a torsional spring, the torsional spring being configured to couple an end of the pathway blockage to an end of the arm, so that the molding material may slide the pathway blockage in one direction, causing the arm to rotate and open the portal and allowing flow of the molding material therethrough, and
the torsional spring being configured to bias the pathway blockage in an opposite direction, causing the arm to rotate and close the portal, and thus restricting flow of the molding material therethrough.

25. The molding system of claim 1, wherein:
the viscous-drag sensor includes:
a screw, and
the actuator includes:
an electric motor being coupled to the screw.

26. The molding system of claim 1, wherein:
the viscous-drag sensor includes:
a screw, and
the actuator includes:
an electric motor being coupled to the screw, the electric motor being configured to turn the screw in one direction while the molding material turns the screw in an opposite direction.

27. The molding system of claim 1, wherein:
the viscous-drag sensor includes:
a screw, and
the actuator includes:
an electric motor being coupled to the screw, the electric motor being configured to turn the screw in one direction while the molding material turns the screw in an opposite direction, and the electric motor includes:
a constant-torque output being connectable to the screw.

28. The molding system of claim 1, wherein:
the viscous-drag sensor includes:
a screw, and
the actuator includes:
a torsional spring being coupled to the screw.

29. The molding system of claim 1, wherein:
the viscous-drag sensor includes:
a screw, and
the actuator includes:
a torsional spring being coupled to the screw, so that the molding material may rotate the screw in one direction while the torsional spring biases the screw in an opposite direction.

30. The molding system of claim 1, wherein:
the viscous-drag sensor includes:
a screw, and
the actuator includes:
a torsional spring being coupled to the screw, the screw defining a portal being closable and openable relative to the melt pathway, so that the molding material may rotate the screw in one direction to open the portal while the torsional spring may bias the screw in an opposite direction to close the portal.

31. The molding system of claim 1, wherein:
the pathway blockage includes:
a body being separate from the pathway blockage; and
a compressible fluid being in fluid contact with the body, and the pathway blockage being in fluid contact with the body.

32. The molding system of claim 1, wherein:
the pathway blockage includes:

a body being separate from the pathway blockage, the body being configured to be slide relative to the melt pathway; and the viscous-drag sensor includes:

a fluid being in fluid contact with the pathway blockage, the pathway blockage being in fluid contact with the body, and the actuator includes:

a compressible fluid being in fluid contact with the pathway blockage, so that the molding material may slide the body in one direction to open the melt pathway and allow flow of the molding material therethrough, while the compressible fluid may bias the body in an opposite direction to close the pathway blockage and restrict flow of the molding material therethrough.

33. The molding system of claim 1, wherein:

the pathway blockage includes:

a body being separate from the pathway blockage, the pathway blockage being in repulsive magnetic contact with the body at an end of the pathway blockage, and the actuator includes:

a magnet being configured to be in repulsive magnetic contact with the pathway blockage on an opposite end of the pathway blockage.

34. The molding system of claim 1, wherein:

the pathway blockage includes:

a body being separate from the pathway blockage, the pathway blockage being in repulsive magnetic contact with the body on an end of the pathway blockage, and the actuator includes:

a magnet being configured to be in repulsive magnetic contact with the pathway blockage on an opposite end of the pathway blockage, so that the molding material may slide the body in one direction to open the passage and allow flow of the molding material therethrough while the body may bias the pathway blockage in an opposite direction to dose the passage and restrict flow of the molding material therethrough.

* * * * *